US010980666B2

(12) United States Patent
Smith et al.

(10) Patent No.: US 10,980,666 B2
(45) Date of Patent: *Apr. 20, 2021

(54) DEVICES AND METHODS FOR VESTIBULAR AND/OR CRANIAL NERVE STIMULATION

(71) Applicant: Scion NeuroStim, LLC, Raleigh, NC (US)

(72) Inventors: Lanty L. Smith, Raleigh, NC (US); Lesco L. Rogers, Raleigh, NC (US)

(73) Assignee: Scion Neurostim, LLC, Raleigh, NC (US)

(*) Notice: Subject to any disclaimer, the term of this patent is extended or adjusted under 35 U.S.C. 154(b) by 68 days.

This patent is subject to a terminal disclaimer.

(21) Appl. No.: 16/004,790

(22) Filed: Jun. 11, 2018

(65) Prior Publication Data

US 2019/0117449 A1 Apr. 25, 2019

Related U.S. Application Data

(63) Continuation of application No. 14/099,059, filed on Dec. 6, 2013, now Pat. No. 9,993,366, which is a (Continued)

(51) Int. Cl.
*A61B 18/18* (2006.01)
*A61F 7/12* (2006.01)
*A61F 7/00* (2006.01)

(52) U.S. Cl.
CPC ............... *A61F 7/12* (2013.01); *A61F 7/007* (2013.01); *A61F 2007/0005* (2013.01);
(Continued)

(58) Field of Classification Search
CPC ...... A61F 2007/0005; A61F 2007/0075; A61F 2007/0093; A61F 2007/0096; A61F 7/007; A61F 7/12
See application file for complete search history.

(56) References Cited

U.S. PATENT DOCUMENTS 4,449,528 A 5/1984 Auth et al.
4,860,748 A 8/1989 Chiurco et al.
(Continued)

FOREIGN PATENT DOCUMENTS

DE 10065592 7/2002
JP H08-195997 7/1996
(Continued)

OTHER PUBLICATIONS

Bock et al. "Vestibular Adaptation to Long-Term Stimuli", Biological Cybernetics, 33, 77-79 (1979).
(Continued)

*Primary Examiner* — Michael F Peffley
*Assistant Examiner* — Amanda L Zink
(74) *Attorney, Agent, or Firm* — Myers Bigel, P.A.

(57) ABSTRACT

An in-ear stimulator for administering thermal stimulation to the ear canal of a subject includes (a) an earpiece configured to be insertable into the ear canal of said subject, the earpiece having an outer surface and an internal cavity formed therein, the internal cavity having an inner surface; and (b) at least one thermoelectric device thermally coupled to the earpiece internal cavity inner surface.

18 Claims, 19 Drawing Sheets

Related U.S. Application Data continuation of application No. 12/970,347, filed on Dec. 16, 2010, now Pat. No. 8,603,152.

(60) Provisional application No. 61/287,873, filed on Dec. 18, 2009, provisional application No. 61/303,984, filed on Feb. 12, 2010, provisional application No. 61/304,059, filed on Feb. 12, 2010.

(52) U.S. Cl.
CPC ............ *A61F 2007/0075* (2013.01); *A61F 2007/0093* (2013.01); *A61F 2007/0096* (2013.01)

(56) References Cited

U.S. PATENT DOCUMENTS

| | | | |
|---|---|---|---|
| 4,918,757 A | 4/1990 | Janssen et al. | |
| 5,190,539 A | 3/1993 | Fletcher et al. | |
| 5,215,086 A | 6/1993 | Terry, Jr. et al. | |
| 5,298,692 A | 3/1994 | Ikeda et al. | |
| 5,871,526 A | 2/1999 | Gibbs et al. | |
| 6,016,449 A | 1/2000 | Fischell et al. | |
| 6,017,337 A | 1/2000 | Pira | |
| 6,300,150 B1 | 10/2001 | Venkatasubramanian | |
| 6,314,324 B1 | 11/2001 | Lattner et al. | |
| 6,511,437 B1 | 1/2003 | Nakamura et al. | |
| 6,746,474 B2 | 6/2004 | Saadat | |
| 6,875,196 B2 | 4/2005 | Abita et al. | |
| 6,882,881 B1 | 4/2005 | Lesser et al. | |
| 6,909,917 B2 | 6/2005 | Woods et al. | |
| 7,189,252 B2* | 3/2007 | Krueger | A61F 7/02 607/104 |
| 7,761,168 B2 | 7/2010 | Gross | |
| 7,856,275 B1* | 12/2010 | Paul | A61N 1/0496 607/55 |
| 7,879,154 B2 | 2/2011 | Warkotsch et al. | |
| 8,083,786 B2 | 12/2011 | Gafni et al. | |
| 8,460,356 B2 | 6/2013 | Rogers et al. | |
| 8,603,152 B2 | 12/2013 | Smith et al. | |
| 8,696,724 B2 | 4/2014 | Rogers | |
| 9,283,111 B2 | 3/2016 | Rogers et al. | |
| 9,655,772 B2 | 5/2017 | Smith et al. | |
| 2002/0072781 A1 | 6/2002 | Lattner et al. | |
| 2003/0097845 A1 | 5/2003 | Saunders et al. | |
| 2003/0158589 A1 | 8/2003 | Katsnelson | |
| 2003/0195588 A1* | 10/2003 | Fischell | A61N 2/02 607/55 |
| 2004/0102525 A1* | 5/2004 | Kozachuk | A61P 25/28 514/662 |
| 2005/0107682 A1 | 5/2005 | Rao et al. | |
| 2005/0165460 A1 | 7/2005 | Erfan | |
| 2006/0095088 A1 | 5/2006 | De Ridder | |
| 2007/0083097 A1 | 4/2007 | Fujiwara et al. | |
| 2007/0087780 A1 | 4/2007 | Nassimi | |
| 2007/0135880 A1 | 6/2007 | Eggers et al. | |
| 2007/0167985 A1 | 7/2007 | Kirby | |
| 2007/0198063 A1 | 8/2007 | Hunter et al. | |
| 2007/0203539 A1 | 8/2007 | Stone et al. | |
| 2007/0225781 A1 | 9/2007 | Saadat et al. | |
| 2007/0250119 A1 | 10/2007 | Tyler et al. | |
| 2007/0265524 A1 | 11/2007 | Eda et al. | |
| 2008/0097549 A1 | 4/2008 | Colbaugh et al. | |
| 2008/0154334 A1 | 6/2008 | Gavronsky | |
| 2008/0182399 A1 | 7/2008 | Cho | |
| 2008/0264464 A1* | 10/2008 | Lee | A61F 7/007 136/201 |
| 2009/0082831 A1 | 3/2009 | Paul et al. | |
| 2009/0182399 A1* | 7/2009 | Sylvestre | A61F 7/12 607/99 |
| 2010/0198204 A1 | 8/2010 | Rogers et al. | |
| 2010/0198282 A1 | 8/2010 | Rogers | |
| 2010/0198318 A1* | 8/2010 | Rogers | A61F 7/007 607/99 |
| 2010/0211142 A1 | 8/2010 | Rogers et al. | |
| 2011/0313498 A1 | 12/2011 | Rogers et al. | |
| 2011/0313499 A1 | 12/2011 | Smith et al. | |
| 2012/0078337 A1 | 3/2012 | Darley et al. | |
| 2012/0310313 A1 | 12/2012 | Rogers et al. | |
| 2012/0316624 A1 | 12/2012 | Smith et al. | |

FOREIGN PATENT DOCUMENTS

| | | |
|---|---|---|
| JP | H08185997 | 7/1996 |
| JP | 09-285468 | 11/1997 |
| JP | H09285468 | 11/1997 |
| JP | 2002-123456 | 5/2002 |
| JP | 2006-0102258 | 4/2006 |
| JP | 2006102258 | 4/2006 |
| JP | 2007-144057 | 6/2007 |
| WO | 00/66215 | 4/2002 |
| WO | 2002/064069 | 8/2002 |
| WO | 2006/079484 | 8/2006 |
| WO | 2009/020862 | 2/2009 |
| WO | 2010/029536 | 3/2010 |
| WO | 2012/083126 | 6/2012 |

OTHER PUBLICATIONS

Brookler, "Simultaneous Bilateral Bithermal Caloric Stimulation in Electronystagmography," Presented at the Meeting of the Eastern Section of the American Laryngological Rhinological and Otological Society, Inc., Britannia Beach Hotel, Paradise Island, Nassau, Jan. 17, 1971.
Extended European Search Report Corresponding to European Application No. 14163419.6, dated Jan. 8, 2015; 3 Pages.
International Preliminary Report on Patentability and Written Opinion of the International Searching Authority for PCT/US2010/060764 dated Jun. 28, 2012.
International Preliminary Report on Patentability for Application No. PCT/US10/60771, dated Jun. 28, 2012.
International Preliminary Report on Patentability for Application No. PCT/US10/60771, dated May 17, 2012.
Miller et al. "Studies of caloric vestibular stimulation: implications for the cognitive neurosciences, the clinical neurosciences and neurophilosophy", Acta Neuropsychiatrica, 19:183-203, (2007).
Ramachandran et al. "Rapid Relief of Thalamic Pain Syndrome Induced by Vestibular Caloric Stimulation", Neurocase, 1-4, Jun. 21, 2007.
Rode et al. "Bilateral vestibular stimulation does not improve visual hemineglect", Neuropsychologia, 40:1104-1106, (2002).
Shinji Nishizawa, "Intervals for Successive Caloric Irrigations", Equilibrium Research, Japan Society for Equilibrium Research, 2001, vol. 60, p. 86-92.
The International Search Report and Written Opinion for PCT/US2010/060771 dated Feb. 22, 2011.
Vincenzo Marcelli et al; "Spano-temporal pattern of vestibular information processing after brief caloric stimulation"; (2008)EJR (European Journal of Radiology) Elsevier EURR-3758; No. of pages 5.
Zhang Na, et al; "Change of extracellular ascorbic acid in the brain cortex following ice water vestibular stimulation: an on-line electrochemical detection coupled with in vivo microdialysis sampling for guinea pigs"; Chin Med J. 2008:121 (12): 1120-1125.
Australian Examination Report Corresponding to Australian Patent Application No. 2008284042; dated Oct. 9, 2012; 3 Pages.
International Preliminary Report on Patentability Corresponding to International Application No. PCT/US2011/065328; dated Jun. 27, 2013; 12 Pages.
International Preliminary Report on Patentability Corresponding to International Application No. PCT/US2011/065321; dated Jun. 27, 2013; 9 Pages.
International Preliminary Report on Patentability Corresponding to International Application No. PCT/US2011/065396; dated Jun. 27, 2013; 7 Pages.
International Preliminary Report on Patentability Corresponding to International Application No. PCT/US2011/065338; dated Jun. 27, 2013; 7 Pages.

(56) References Cited

OTHER PUBLICATIONS

International Preliminary Report on Patentability Corresponding to International Application No. PCT/US2011/065456; dated Jun. 27, 2013; 8 Pages.
International Preliminary Report on Patentability Corresponding to International Application No. PCT/US2010/060764, dated Jun. 28, 2012; 9 Pages.
International Search Report and Written Opinion Corresponding to International Application No. PCT/US2011/065328; dated Mar. 29, 2012; 13 Pages.
International Search Report and Written Opinion Corresponding to International Application No. PCT/US2011/065321; dated Mar. 29, 2012; 10 Pages.
International Search Report and Written Opinion Corresponding to International Application No. PCT/US2011/065396; dated Apr. 23, 2012; 8 Pages.
International Search Report and Written Opinion Corresponding to International Application No. PCT/US2011/065338; dated Apr. 20, 2012; 8 Pages.
International Search Report and Written Opinion Corresponding to International Application No. PCT/US2011/065456; dated Apr. 4, 2012; 9 Pages.
International Search Report and Written Opinion Corresponding to International Application No. PCT/US2010/060764; dated Feb. 22, 2011.
Japanese Office Action Corresponding to Japanese Patent Application No. 2010-519241; dated Dec. 7, 2012; Foreign Text, 5 Pages, English Translation Thereof, 4 Pages.

\* cited by examiner

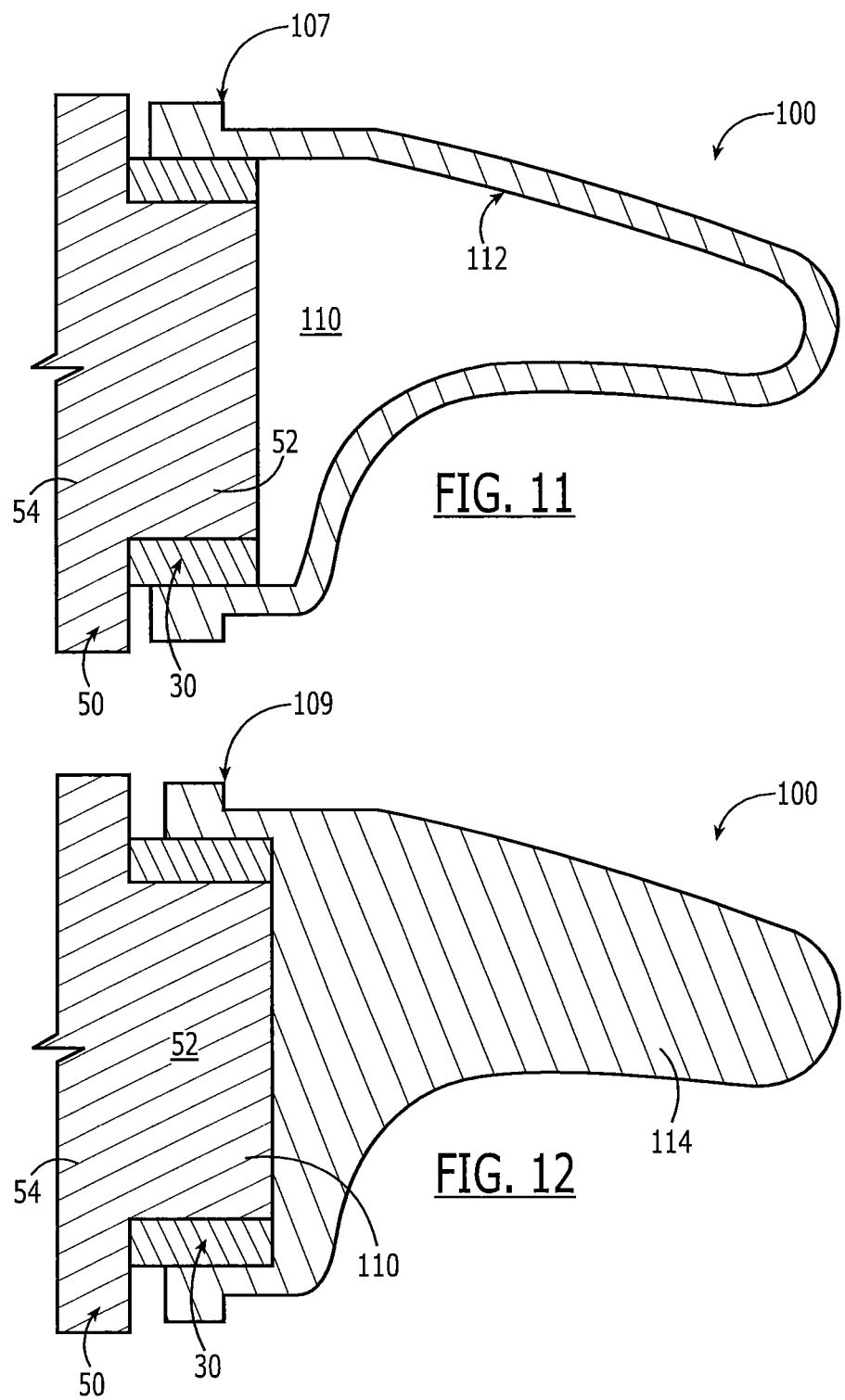

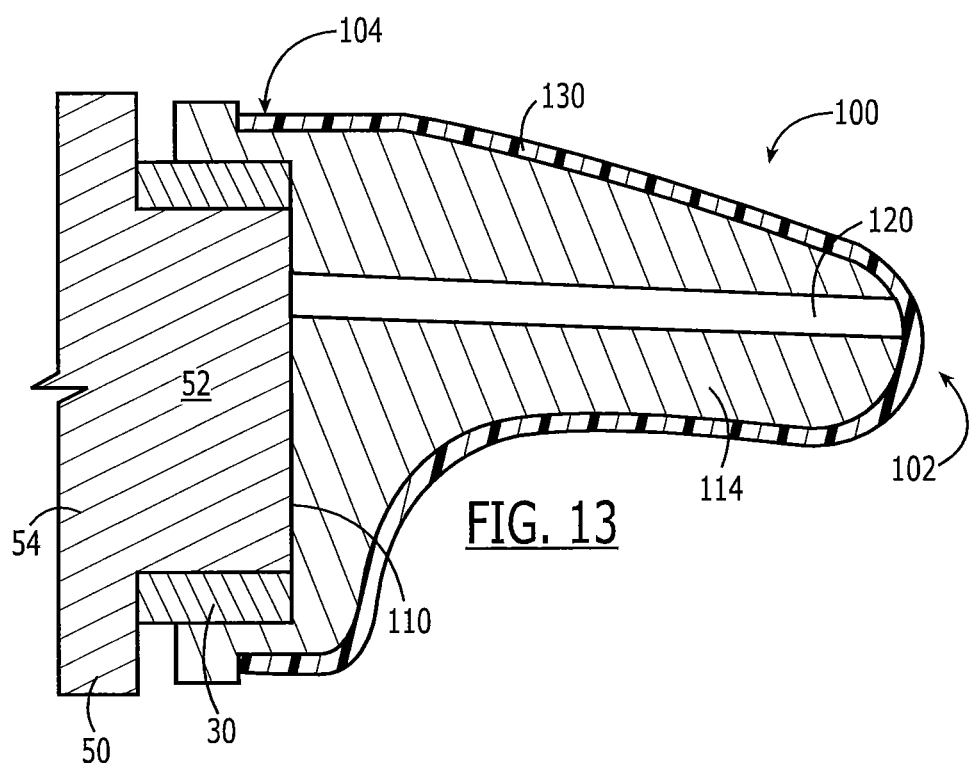

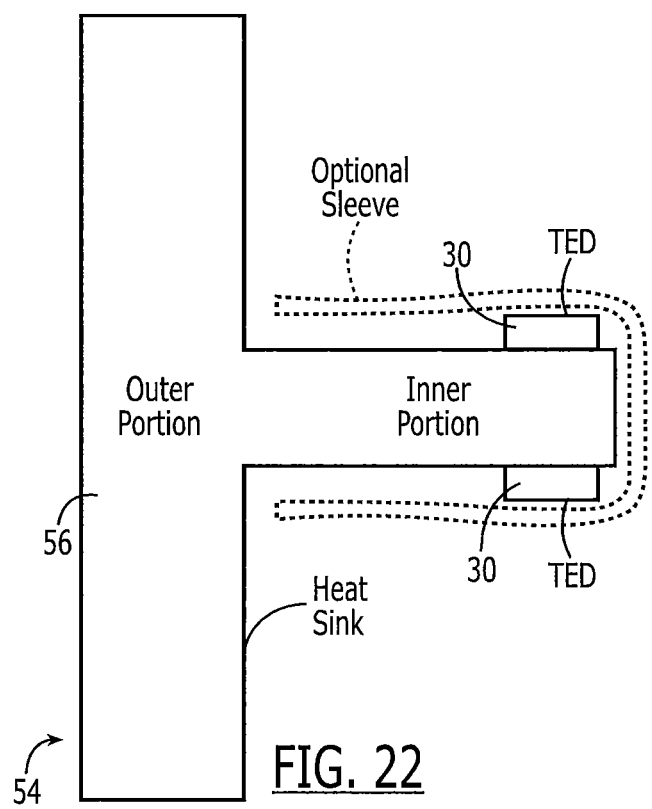

DEVICES AND METHODS FOR VESTIBULAR AND/OR CRANIAL NERVE STIMULATION

RELATED APPLICATIONS

This application is a continuation of U.S. patent application Ser. No. 14/099,059, now U.S. Pat. No. 9,993,366, filed Dec. 6, 2013, which is a continuation of U.S. patent application Ser. No. 12/970,347, now U.S. Pat. No. 8,603,152, filed Dec. 16, 2010 which claims priority to (a) United States Provisional Application No. 61/287,873, filed Dec. 18, 2009; (b) U.S. Provisional Application No. 61/303,984, filed Feb. 12, 2010; and (c) U.S. Provisional Patent No. 61/304,059, filed Feb. 12, 2010 and is related to (a) U.S. patent application Ser. No. 12/669,684, now U.S. Pat. No. 8,262,717, Ser. No. 12/699,374, now U.S. Pat. No. 8,267,984, Ser. No. 12/704,872, now U.S. Pat. No. 8,696,724, Ser. No. 11/972,267, Ser. No. 12/166,953 and Ser. No. 12/693,016, now U.S. Pat. No. 8,267,983, (b) U.S. Provisional Application Nos. 60/884,546, 60/908,261, 60/953,700 and 61/224,668; (c) PCT Application No. PCT/US2008/071935, the disclosure of each of which is incorporated herein by reference in its entirety.

FIELD OF THE INVENTION

The present invention relates to apparatuses and associated methods useful for delivering stimulation to the nervous system and/or the vestibular system of an individual, thereby inducing physiological changes in the individual and/or treating a disorder or symptom of the individual.

BACKGROUND

Caloric vestibular stimulation ("CVS") has long been known as a diagnostic procedure for testing the function of the vestibular system. In the traditional hospital setting, water caloric tests are used to assess levels of consciousness during acute or chronic brain injury. The brain injury may be due to head trauma or a central nervous system event such as a stroke. Other brain injuries occur in the presence of metabolic abnormalities (e.g., kidney disease, diabetes), seizures, or toxic levels of controlled substances or alcohol.

U.S. Patent Publication No. 2003/0195588 to Fischell et al. discusses a stimulator in an ear canal that is adapted to provide magnetic, electrical, audible, tactile or caloric stimulation. Fischell proposes a ring-shaped caloric transducer strip on an ear canal sensor/stimulator system that may result in relatively slow thermal changes of the ear canal.

Accordingly, apparatuses and associated methods useful for delivering stimulation to the nervous system and/or the vestibular system of an individual that may be capable of relatively fast temperature changes are potentially beneficial to take full advantage of physiological responses that are useful in diagnosing and/or treating a variety of medical conditions.

SUMMARY OF EMBODIMENTS OF THE INVENTION

According to some embodiments, an in-ear stimulator for administering thermal stimulation to the ear canal of a subject includes (a) an earpiece configured to be insertable into the ear canal of the subject, the earpiece having an outer surface and an internal cavity formed therein, the internal cavity having an inner surface; and (b) at least one thermoelectric device thermally coupled to the earpiece internal cavity inner surface.

In some embodiments, the stimulator further comprising a heat sink positioned in the earpiece internal cavity, wherein the heat sink is thermally coupled to the at least one thermoelectric device. The heat sink may include an inner portion extending into the earpiece and having a generally planar surface. The earpiece internal surface may have a corresponding cooperating planar surface, and the at least one thermoelectric device may be mounted between the heat sink planar surface and the cooperating portion of the earpiece inner surface. The heat sink may include a side portion that generally conforms to a corresponding side portion of the inner surface of the internal cavity. The at least one thermoelectric device may be mounted between the side portion of the heat sink and the side portion of the inner surface of the internal cavity.

In some embodiments, the heat sink includes an inner portion received in the earpiece internal cavity, and a shape of the inner portion substantially corresponds to a shape of the internal cavity. The heat sink may include an outer portion positioned outside of the earpiece internal cavity. The heat sink outer portion may includes a plurality of fins. The heat sink may be formed of aluminum and may have a weight between about 30 grams and about 70 grams.

In some embodiments, the earpiece is formed from a rigid, thermally-conductive material. In some embodiments, the earpiece comprises aluminum. In some embodiments, earpiece weighs about 9 grams or less. In some embodiments, the earpiece weighs about 4 grams or less.

In some embodiments, the at least one thermoelectric device comprises a plurality of thermoelectric devices. In some embodiments, the plurality of thermoelectric devices are thermally coupled to one another.

In some embodiments, the at least one thermoelectric device comprises a thin film thermoelectric device.

In some embodiments, the earpiece is thermally coupled to a first side of the at least one thermoelectric device and the heat sink is thermally coupled to a second side of the at least one thermoelectric device.

In some embodiments, the earpiece is conical in shape. The earpiece may include a circular cone. The earpiece may include a conical apex of the conical shape that has been blunted to form a dome-shaped point. The earpiece may include a generally cylindrical base having opposite first and second ends, and the base may define a longitudinal centerline. An extended portion may extend from the second end of the cylindrical base, and the dome-shaped point may be offset from the longitudinal centerline. The cross-sectional area of the extended portion may decrease as a function of distance away from the base. The extended portion may taper unevenly from the cylindrical base to the dome-shaped point.

In some embodiments, the stimulator includes a head piece, and the head piece is configured for positioning the earpiece in the ear canal of the subject.

In some embodiments, an in-ear stimulator for administering thermal stimulation to the ear canals of a subject includes: (a) a first earpiece configured to be insertable into the right ear canal of the subject, the first earpiece having an outer surface and an internal cavity formed therein, the internal cavity having an inner surface; (b) a second earpiece configured to be insertable into the left ear canal of the subject, the second earpiece having an outer surface and an internal cavity formed therein, the internal cavity having an inner surface; (c) at least one thermoelectric device thermally coupled to the first earpiece internal cavity; (d) at least one thermoelectric device thermally coupled to the second earpiece internal cavity; and (e) a headpiece configured to position the first earpiece in the right ear canal of the subject and to position the second earpiece in the left ear canal of the subject.

In some embodiments, the headpiece comprises a flexible or adjustable, band.

In some embodiments, the stimulator includes a first heat sink positioned in the first earpiece internal cavity, and the first heat sink is thermally coupled to the at least one thermoelectric device coupled to the first earpiece internal cavity. The stimulator further includes a second heat sink positioned in the second earpiece internal cavity, and the second heat sink is thermally coupled to the at least one thermoelectric device coupled to the first earpiece internal cavity. In some embodiments, the first heat sink comprises an inner portion extending into the first earpiece and having a generally planar surface. The first earpiece internal surface has a corresponding cooperating planar surface, and the at least one thermoelectric device is mounted between the first heat sink planar surface and the cooperating portion of the first earpiece inner surface. The second heat sink includes an inner portion extending into the first earpiece and having a generally planar surface, and the second earpiece internal surface has a corresponding cooperating planar surface. The at least one thermoelectric device is mounted between the second heat sink planar surface and the cooperating portion of the second earpiece inner surface.

In some embodiments, methods for delivering caloric stimulation to a subject include positioning at least a portion of an in-ear stimulator in an ear canal of the subject. The in-ear stimulator includes (a) an earpiece configured to be insertable into the ear canal of the subject, the earpiece having an outer surface and an internal cavity formed therein, the internal cavity having an inner surface; and (b) at least one thermoelectric device thermally coupled to the earpiece internal cavity inner surface. A time-varying thermal waveform is delivered to the at least one thermoelectric device such that the thermoelectric device effects corresponding temperature changes to the earpiece to deliver caloric stimulation to the subject.

In some embodiments, the stimulator further comprises a heat sink positioned in the earpiece internal cavity, and the heat sink is thermally coupled to the at least one thermoelectric device. The heat sink may include an inner portion extending into the earpiece and having a generally planar surface, and the earpiece internal surface may have a corresponding cooperating planar surface. The at least one thermoelectric device is mounted between the heat sink planar surface and the cooperating portion of the earpiece inner surface.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 11 is a side-cross sectional view of the earpiece, TEDs, and heat sink of FIG. 9.

FIG. 12 is a side-cross sectional view of an earpiece, TEDs and heat sink according to some embodiments of the present invention.

FIG. 13 is a side-cross sectional view of an earpiece, TEDs and heat sink according to some embodiments of the present invention.

FIG. 22 is a schematic diagram of a heat sink and thermoelectric device according to some embodiments of the present invention.

DETAILED DESCRIPTION OF EMBODIMENTS OF THE INVENTION

Figure 1:
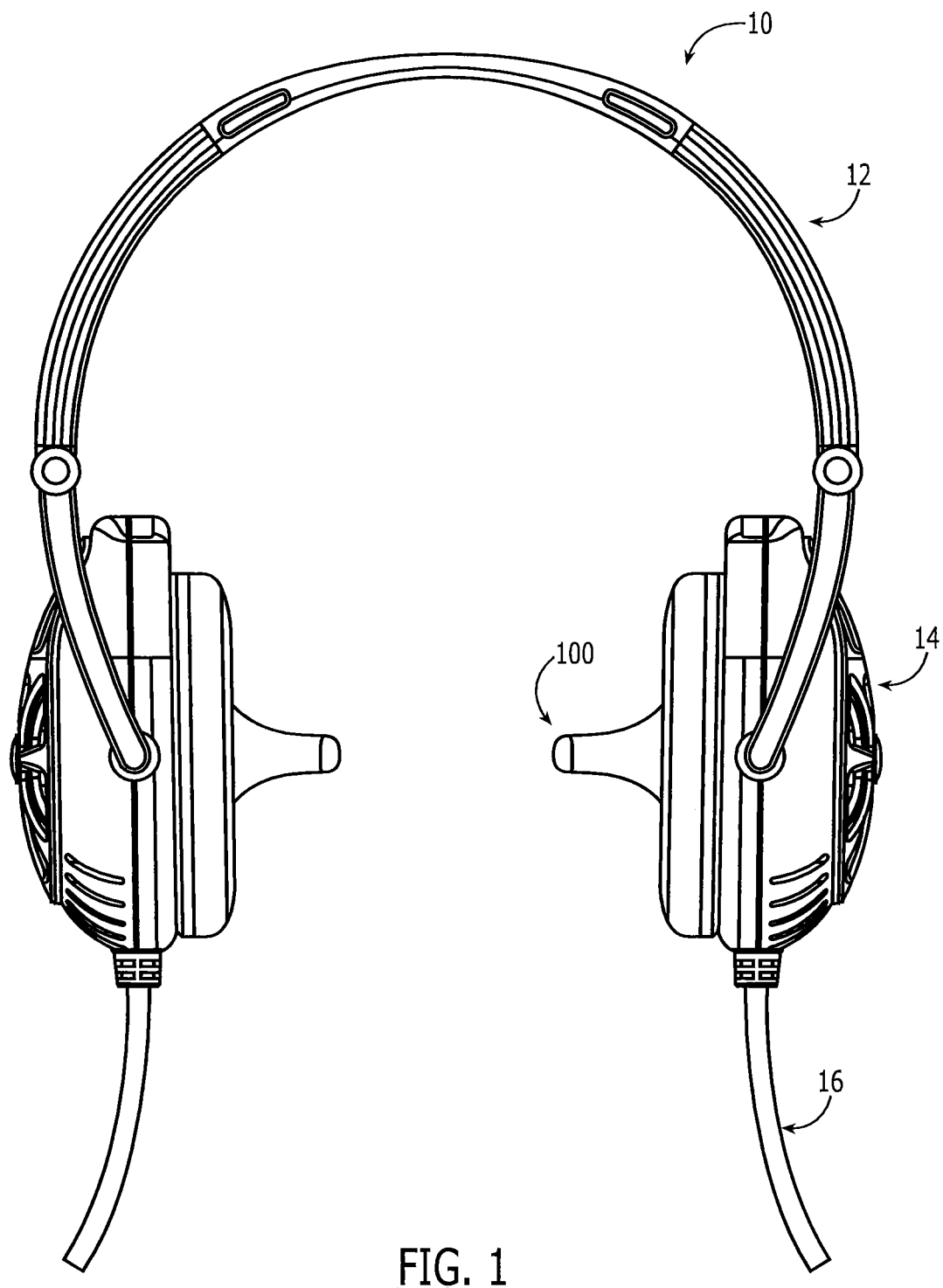
FIG. 1 is a front view of an in-ear stimulation apparatus according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the term "vestibular system" has the meaning ascribed to it in the medical arts and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

"Treatment," "treat," and "treating" refer to reversing, alleviating, reducing the severity of, delaying the onset of, inhibiting the progress of, or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event), hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve. Treatment may be as an adjuvant treatment as further described herein.

"Adjuvant treatment" as described herein refers to a treatment session in which the patient benefit is reducing or eliminating the need for another medication or treatment, such as a drug treatment or electrical stimulus.

"Chronic treatment," "Chronically treating," or the like refers to a therapeutic treatment carried out at least 2 to 3 times a week (or in some embodiments at least daily) over an extended period of time (typically at least one to two weeks, and in some embodiments at least one to two months), for as long as required to achieve and/or maintain therapeutic efficacy for the particular condition or disorder for which the treatment is carried out.

"Waveform" or "waveform stimulus" as used herein refers to the thermal stimulus (heating, cooling) delivered to the ear canal of a subject through a suitable apparatus to carry out the methods described herein. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying waveforms are preferred over square waveforms in carrying out the present invention.

In general, a waveform stimulus used to carry out the present invention comprises a leading edge, a peak, and a trailing edge. If a first waveform stimulus is followed by a second waveform stimulus, then the minimal stimulus point therebetween is referred to as a trough.

The first waveform of a treatment session is initiated at a start point, which start point may be the at or about the subject's body temperature at the time the treatment session is initiated (typically a range of about 34 to 38 degrees Centigrade, around a normal body temperature of about 37 degrees Centigrade. The lower point, 34, is due to the coolness of the ear canal. It typically will not be above about 37 unless the patient is febrile). Note that, while the subject's ear canal may be slightly less than body temperature (e.g., about 34 to 36 degrees Centigrade), the starting temperature for the waveform is typically body temperature (the temp of the inner ear), or about 37 degrees Centigrade. In some embodiments, however, the temperature of the treatment device may not have equilibrated with the ear canal prior to the start of the treatment session, and in such case the start point for at least the first waveform stimulus may be at a value closer to room temperature (about 23 to 26 degrees Centigrade).

The waveform leading edge is preferably ramped or time-varying: that is, the amplitude of the waveform increases through a plurality of different temperature points over time (e.g., at least 5, 10, or 15 or more distinct temperature points, and in some embodiments at least 50, 100, or 150 or more distinct temperature points, from start to peak). The shape of the leading edge may be a linear ramp, a curved ramp (e.g., convex or concave; logarithmic or exponential), or a combination thereof. A vertical cut may be included in the waveform leading edge, so long as the remaining portion of the leading edge progresses through a plurality of different temperature points over time as noted above.

The peak of the waveform represents the amplitude of the waveform as compared to the subject's body temperature. In general, an amplitude of at least 5 or 7 degrees Centigrade is preferred for both heating and cooling waveform stimulation. In general, an amplitude of up to 20 degrees Centigrade is preferred for cooling waveform stimulation. In general, an amplitude of up to 8 or 10 degrees Centigrade is preferred for heating waveform stimulus. The peak of the waveform may be truncated (that is, the waveform may reach an extended temperature plateau), so long as the desired characteristics of the leading edge, and preferably trailing edge, are retained. For heating waveforms, truncated peaks of long duration (that is, maximum heat for a long duration) are less preferred, particularly at higher heats, due to potential burning sensation.

The waveform trailing edge is preferably ramped or time-varying: that is, the amplitude of the waveform decreases through a plurality of different temperature points over time (e.g., at least 5, 10, or 15 or more distinct temperature points, or in some embodiments at least 50, 100, or 150 or more distinct temperature points, from peak to trough). The shape of the trailing edge may be a linear ramp, a curved ramp (e.g., convex or concave; logarithmic or exponential), or a combination thereof. A vertical cut may again be included in the waveform trailing edge, so long as the remaining portion of the trailing edge progresses through a plurality of different temperature points over time as noted above.

The duration of the waveform stimulus (or the frequency of that waveform stimulus) is the time from the onset of the leading edge to either the conclusion of the trailing edge or (in the case of a vertically cut waveform followed by a subsequent waveform). In general, each waveform stimulus has a duration, or frequency, of from one or two minutes up to ten or twenty minutes.

A treatment session may have a total duration of five or ten minutes, up to 20 or 40 minutes or more, depending on factors such as the specific waveform or waveforms delivered, the patient, the condition being treated, etc.

In a treatment session, a plurality of waveforms may be delivered in sequence. In general, a treatment session will comprise 1, 2 or 3 waveforms, up to about 10 or 20 waveforms delivered sequentially. Each individual waveform may be the same, or different, from the other. When a waveform is followed by a subsequent waveform, the minimum stimulus point (minimum heating or cooling) between is referred to as the trough. Like a peak, the trough may be truncated, so long as the desired characteristics of the trailing edge, and the following next leading edge, are retained. While the trough may represent a return to the subject's current body temperature, in some embodiments minor thermal stimulation (cooling or heating; e.g, by 1 or 2 degrees up to 4 or 5 degrees Centigrade) may continue to be applied at the trough (or through a truncated trough).

Treatment sessions are preferably once a day, though in some embodiments more frequent treatment sessions (e.g. two or three times a day) may be employed. Day-to-day treatments may be by any suitable schedule: every day; every other day; twice a week; as needed by the subject, etc. The overall pattern of treatment is thus typically chronic (in contrast to "acute," as used in one-time experimental studies).

Subjects may be treated with the present invention for any reason. In some embodiments, disorders for which treatment may be carried out include, include, but are not limited to, migraine headaches (acute and chronic), depression, anxiety (e.g. as experienced in post-traumatic stress disorder ("PTSD") or other anxiety disorders), spatial neglect, Parkinson's disease, seizures (e.g., epileptic seizures), diabetes (e.g., type II diabetes), etc.

Additional disorders and conditions that can be treated by the methods and systems of the present invention include, but are not limited to, neuropathic pain (e.g., migraine headaches), tinnitus, brain injury (acute brain injury, excitotoxic brain injury, traumatic brain injury, etc.), spinal cord injury, body image or integrity disorders (e.g., spatial neglect), visual intrusive imagery, neuropsychiatric disorders (e.g. depression), bipolar disorder, neurodegenerative disorders (e.g. Parkinson's disease), asthma, dementia, insomnia, stroke, cellular ischemia, metabolic disorders, (e.g., diabetes), post-traumatic stress disorder ("PTSD"), addictive disorders, sensory disorders, motor disorders, and cognitive disorders.

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the subject has two or more of the above conditions, and both conditions are treated concurrently with the methods and systems of the invention. For example, a subject with both depression and anxiety (e.g., PTSD) can be treated for both, concurrently, with the methods and systems of the present invention.

The methods and systems according to embodiments of the present invention utilize thermoelectric devices (TEDs) to induce physiological and/or psychological responses in a subject for medically diagnostic and/or therapeutic purposes. Subjects to be treated and/or stimulated with the methods, devices and systems of the present invention include both human subjects and animal subjects. In particular, embodiments of the present invention may be used to diagnose and/or treat mammalian subjects such as cats, dogs, monkeys, etc. for medical research or veterinary purposes.

As noted above, embodiments according to the present invention utilize TEDs to provide an in-ear stimulator for administering thermal stimulation in the ear canal of the subject. The ear canal serves as a useful conduit to the individual's vestibular system and to the vestibulocochlear nerve. Without wishing to be bound by any particular theory, it is believed that thermal stimulation of the vestibular system is translated into electrical stimulation within the central nervous system ("CNS") and propagated throughout the brain, including but not limited to the brain stem, resulting in certain physiological changes that may be useful in treating various disease states (increased blood flow, generation of neurotransmitters, etc). See, e.g., Zhang, et al. Chinese Medical J 121:12:1120 (2008) (demonstrating increased ascorbic acid concentration in response to cold water CVS).

Figure 2:
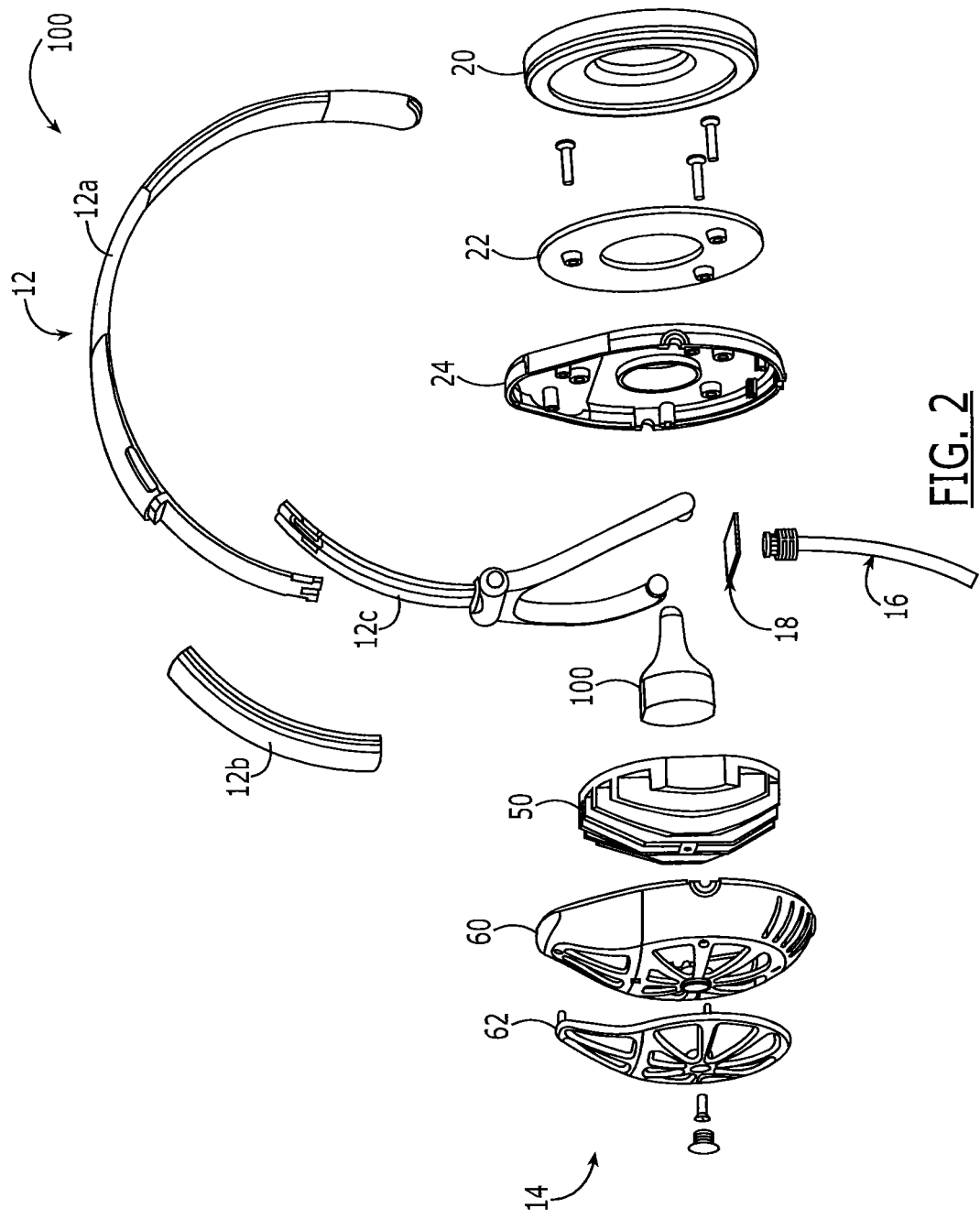
FIG. 2 is an exploded perspective view of one side of the in-ear stimulation apparatus of FIG. 1.
Figure 3:
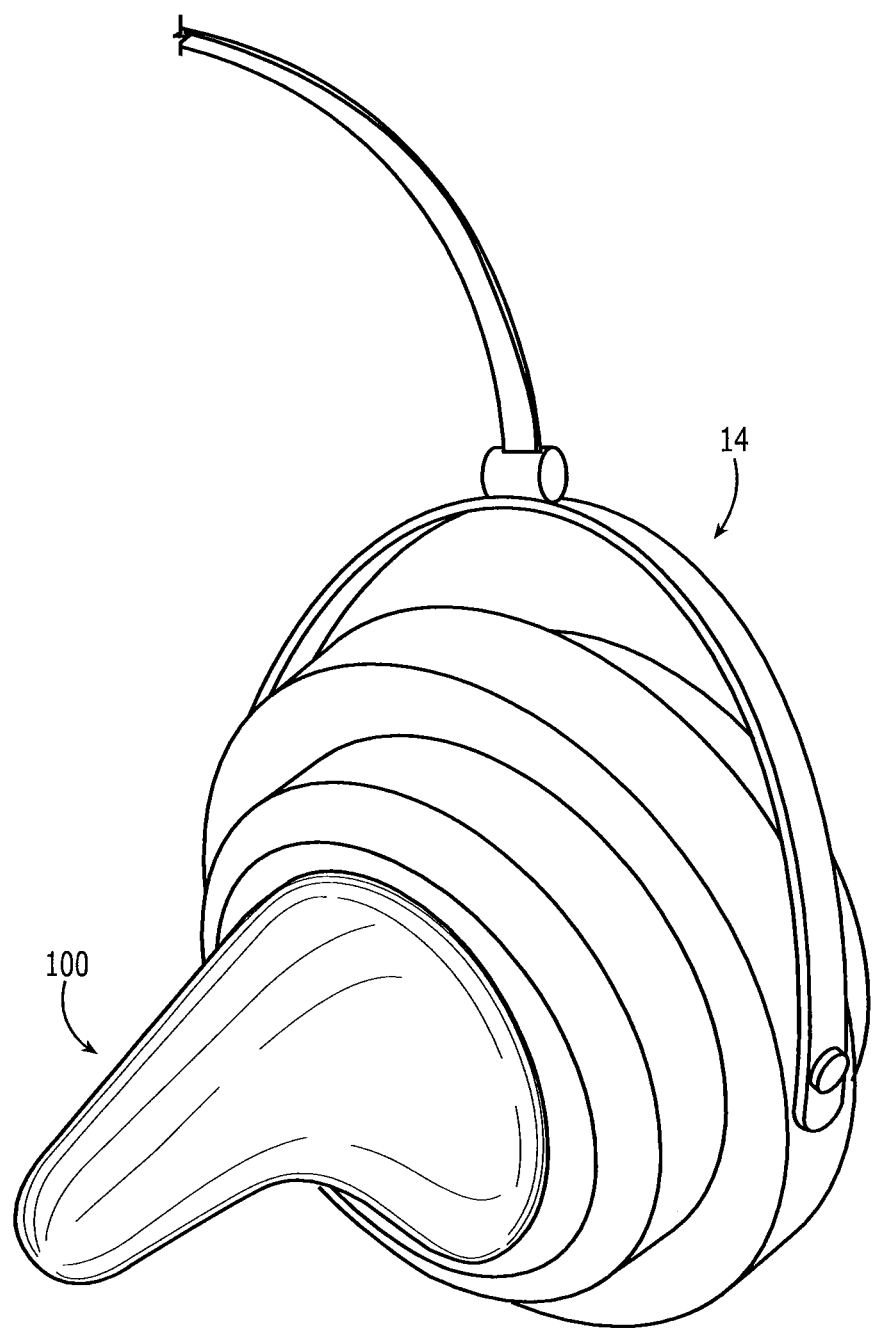
FIG. 3 is a perspective view of the right side of an earpiece and earphones of the in-ear stimulation apparatus of FIG. 1.

As illustrated in FIG. 1-3, an in-ear stimulation apparatus 10 includes a support or headband 12, earphones 14 and a controller and/or power connection or cable 16. The earphones 14 include an earpiece 100 that is configured to be positioned in the ear of a patient or subject. Although embodiments according to the invention are illustrated with respect to two earpieces 100 such that stimulation may be provided in both ears, it should be understood that the in-ear stimulation apparatus 10 in some embodiments may omit one of the earpieces 100 to provide in-ear stimulation to one ear of a subject.

As illustrated in FIG. 2, the earphones 14 include a cushion 20 connected to supports 22 and 24, the earpiece 100, a heat sink 50 and two additional, ventilated support members 60 and 62. One or more thermoelectric devices (TEDs) (not shown) may be thermally coupled between the earpiece 100 and the heat sink 50. Thus, the TEDs between the earpiece 100 and the heat sink 50 create a temperature difference between the earpiece 100 and the heat sink 50 when a voltage is applied to the TEDs so that the temperature of the earpiece 100 may be increase and/or decreased. The efficiency with which the temperature of the earpiece 100 is changed may be increased by the heat sink 50, which dissipates excess heat or cold from the side of the TEDs opposite the earpiece 100 into the surrounding environment. As discussed above, the ear canal may serve as a useful conduit to the subject's vestibular system and/or to the vestibulocochlear nerve for thermal stimulation for providing caloric vestibular stimulation (CVS) and/or cranial nerve stimulation.

Thin film TEDs, Peltier coolers/heaters or transducers may be used as transducers in some embodiments, including, but not limited to, the thin film TEDs described in U.S. Pat. No. 6,300,150 and U.S. Patent Publication Nos. 2007/0028956 and 2006/0086118; however, any suitable TED may be used. Such thin film TEDs may also advantageously incorporate a temperature sensing function, so that temperature sensing can be accomplished through the same device without the need for a separate temperature sensor. Thin film TEDs are commercially available from Nextreme Thermal Solutions (Durham, N.C., USA)(e.g., OptoCooler™ Series (UPT40 and UPF4), Eteg™ UPF40) and Micropelt, GmbH (Freiburg, Germany)(e.g., MPC-D303 and MPC-D305). Although embodiments according to the invention are described herein with respect to TEDs, it should be understood that any suitable type of thermal device may be used, including optical heating (e.g., using a laser) and ultrasound heating (e.g., a piezoelectric heating device). TEDs may be provided that include a heat flux of 80-120 W/cm$^2$ or more. TEDs may be generally rectangular in shape, with typical rectangular areas being about 2×1 mm or 5×2 mm or more and having a height profile of 1 mm or 0.65 mm or 0.5 mm or less. The TEDs may be connected in parallel or in series to provide thermal changes to a desired region of an earpiece and/or heat sink.

The headband 12 includes adjustable members 12a-12c in a slideable configuration for adjusting the size of the headband 12 for increased comfort and a better fit. However, it should be understood that other configurations for supporting the headphones may be used, including support bands that are positioned under the chin or over the ear, for example, as may be used with audio earphones. As illustrated, the cushion 20 may be configured to increase comfort and/or the fit of the earpiece 100 in the subject's ear canal. For example, the cushion 20 may be sized or may be adjustable so as to place the earpiece 100 in the ear canal without placing excessive pressure on the eardrum. The cable 16 is connected to a printed circuit board (PCB) 18 at one end and to a controller (not shown) on the opposite end. The PCB 18 may be electrically connected to the TEDs between the earpiece 100 and the heat sink 50 and may provide a power supply and control signals for operating the TEDs, such as control signals to control desired temperatures and temperature changes, from the controller. The earpiece 100 may further include a temperature sensor/controller so that the TEDs may provide a temperature stability, e.g., of about 0.1-0.5° C.

Figure 4:
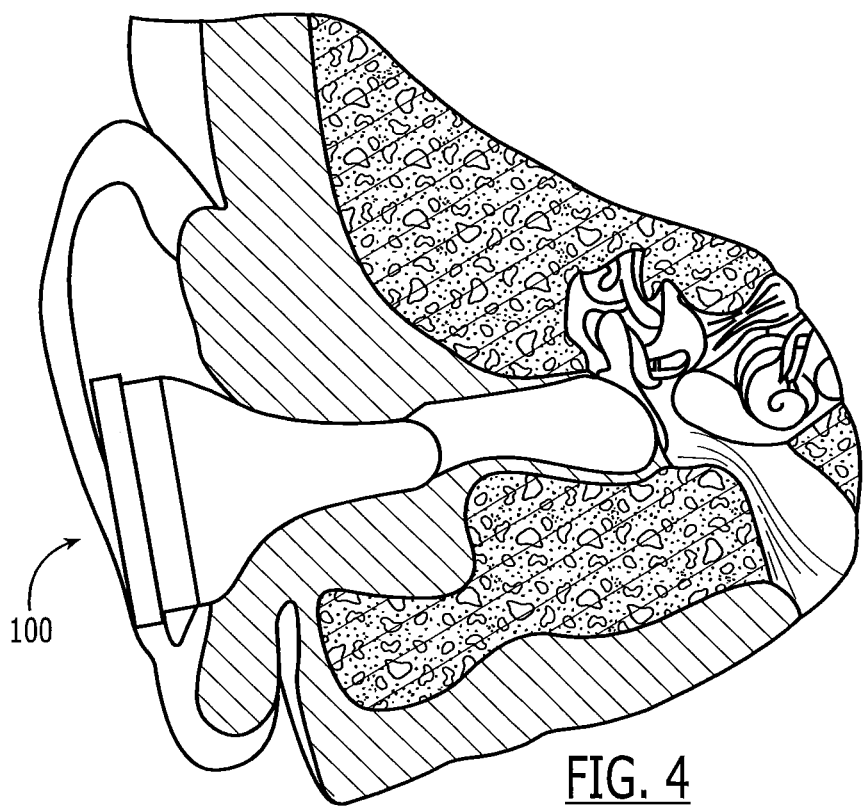
FIG. 4 is a cut-away cross-sectional view of the earpiece of the in-ear stimulation apparatus of FIG. 1 inserted into the ear canal of a subject.
Figure 6D:
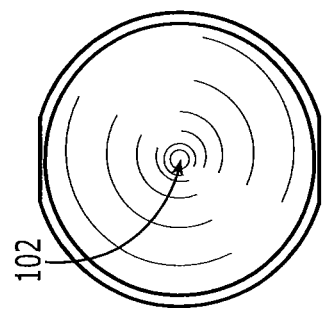
FIG. 6D is a top view of the earpiece of FIG. 6A.

In this configuration, the earpiece 100 may be fit into the subject's ear as shown, e.g., in FIG. 4 (the anatomical portion of the figures is adapted from FIG. 2 of U.S. Pat. No. 4,244,377). The earpiece 100 is so dimensioned as to be insertable into the ear canal of the subject. As illustrated, the earpiece 100 may intimately contact the ear canal so as to thermally stimulate the temporal bone in the distal portion of the external auditory meatus.

As illustrated in FIG. 5A-5D, the earpiece 100 may have an generally conical shape including a rounded tip portion 102, a generally circular base portion 104, a back facing side 106 (which faces the back side of the subject after insertion in the ear canal) and a front facing side 108 (which faces the front or face of the subject after insertion in the ear canal). As shown, for example, in FIG. 5D, the tip portion 102 may be blunted to form a dome-shaped point. The base portion 104 defines a longitudinal centerline in the center of the base portion 104, and the cross section of the earpiece 100 decreases as a function of distance away from the base portion 104. As illustrated, the cross section of the earpiece 100 tapers unevenly from the base portion 104 to the tip portion 102. Thus, the tip portion 102 (which extends from the base portion 104) is off-set from the centerline of the base portion 104, e.g., by about 10° to about 40° from a vertical axis, to provide an improved fit in the ear canal of the subject. In some embodiments, the tip portion 102 is off-set from the center of the earpiece 100 in a direction toward the front facing side 108.

Figure 5D:
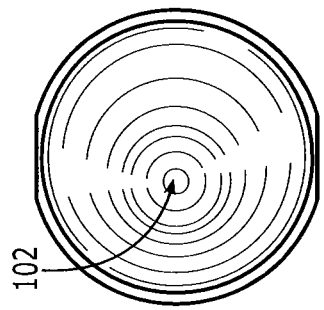
FIG. 5D is a top view of the earpiece of the in-ear stimulation apparatus of FIG. 1.
Figure 5C:
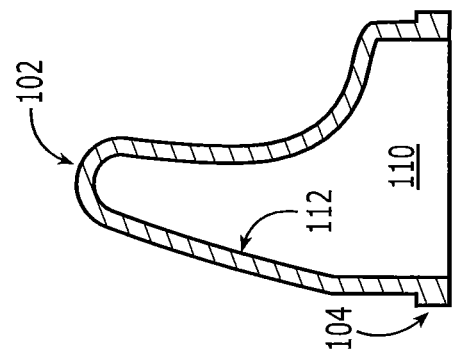
FIG. 5C is a side cross-sectional view of the earpiece of the in-ear stimulation apparatus of FIG. 1.
Figure 6C:
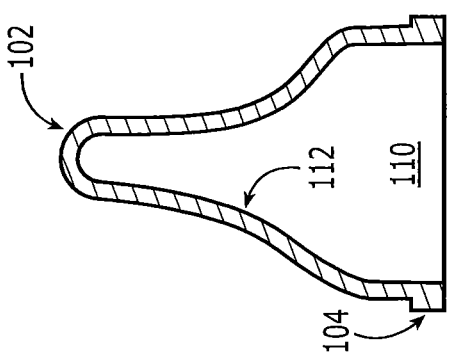
FIG. 6C is a side cross-sectional view of the earpiece of FIG. 6A.
Figure 5B:
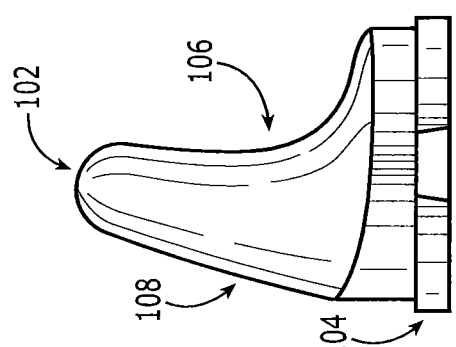
FIG. 5B is a side view of the earpiece of the in-ear stimulation apparatus of FIG. 1.
Figure 6B:
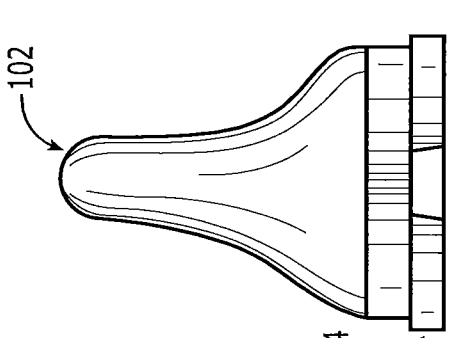
FIG. 6B is a side view of the earpiece of FIG. 6A.
Figure 5A:
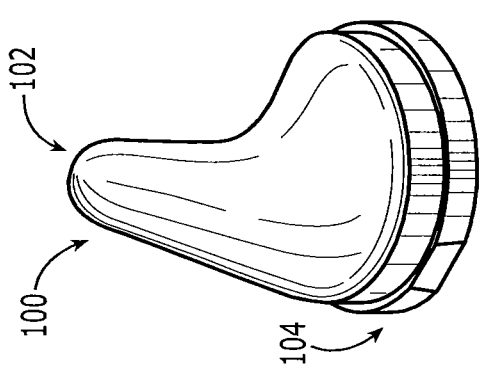
FIG. 5A is a perspective view of the earpiece of the in-ear stimulation apparatus of FIG. 1.
Figure 6A:
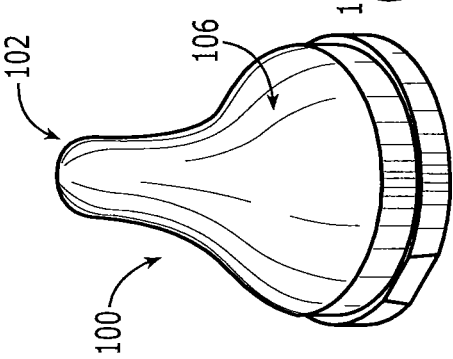
FIG. 6A is a side perspective view of an earpiece for in-ear stimulation according to some embodiments of the present invention.
Figure 7D:
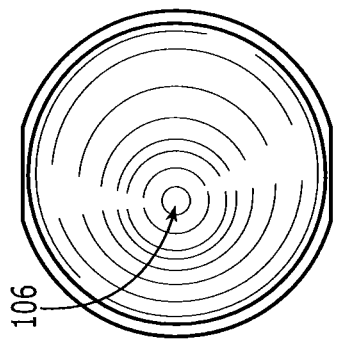
FIG. 7D is a top view of the earpiece of FIG. 7A.
Figure 8D:
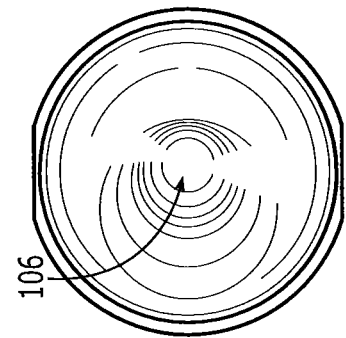
FIG. 8D is a top view of the earpiece of FIG. 8A.
Figure 7C:
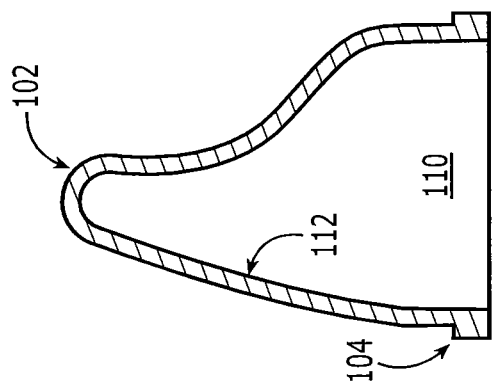
FIG. 7C is a side cross-sectional view of the earpiece of FIG. 7A.
Figure 8C:
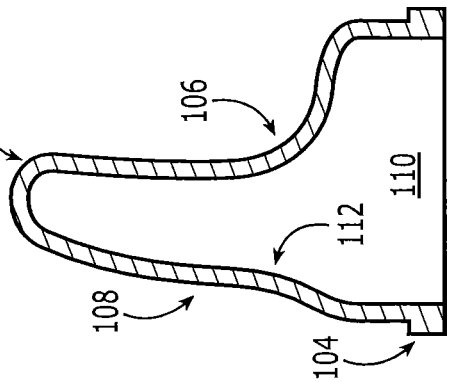
FIG. 8C is a side cross-sectional view of the earpiece of FIG. 8A.
Figure 7B:
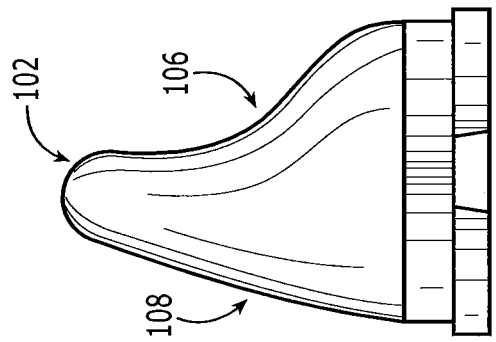
FIG. 7B is a side view of the earpiece of FIG. 7A.
Figure 8B:
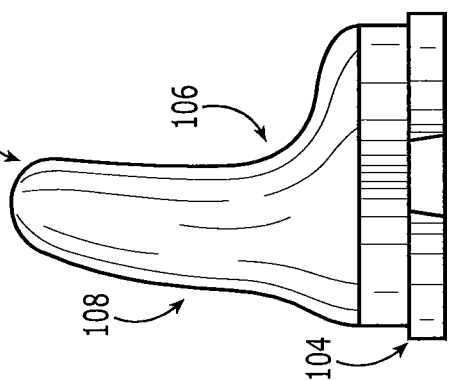
FIG. 8B is a side view of the earpiece of FIG. 8A.
Figure 7A:
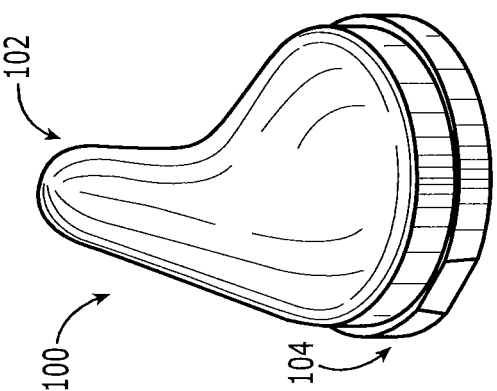
FIG. 7A is a side perspective view of an earpiece for in-ear stimulation according to some embodiments of the present invention.
Figure 8A:
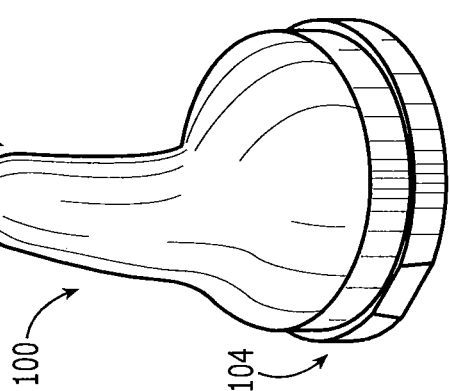
FIG. 8A is a side perspective view of an earpiece for in-ear stimulation according to some embodiments of the present invention.
Figure 9:
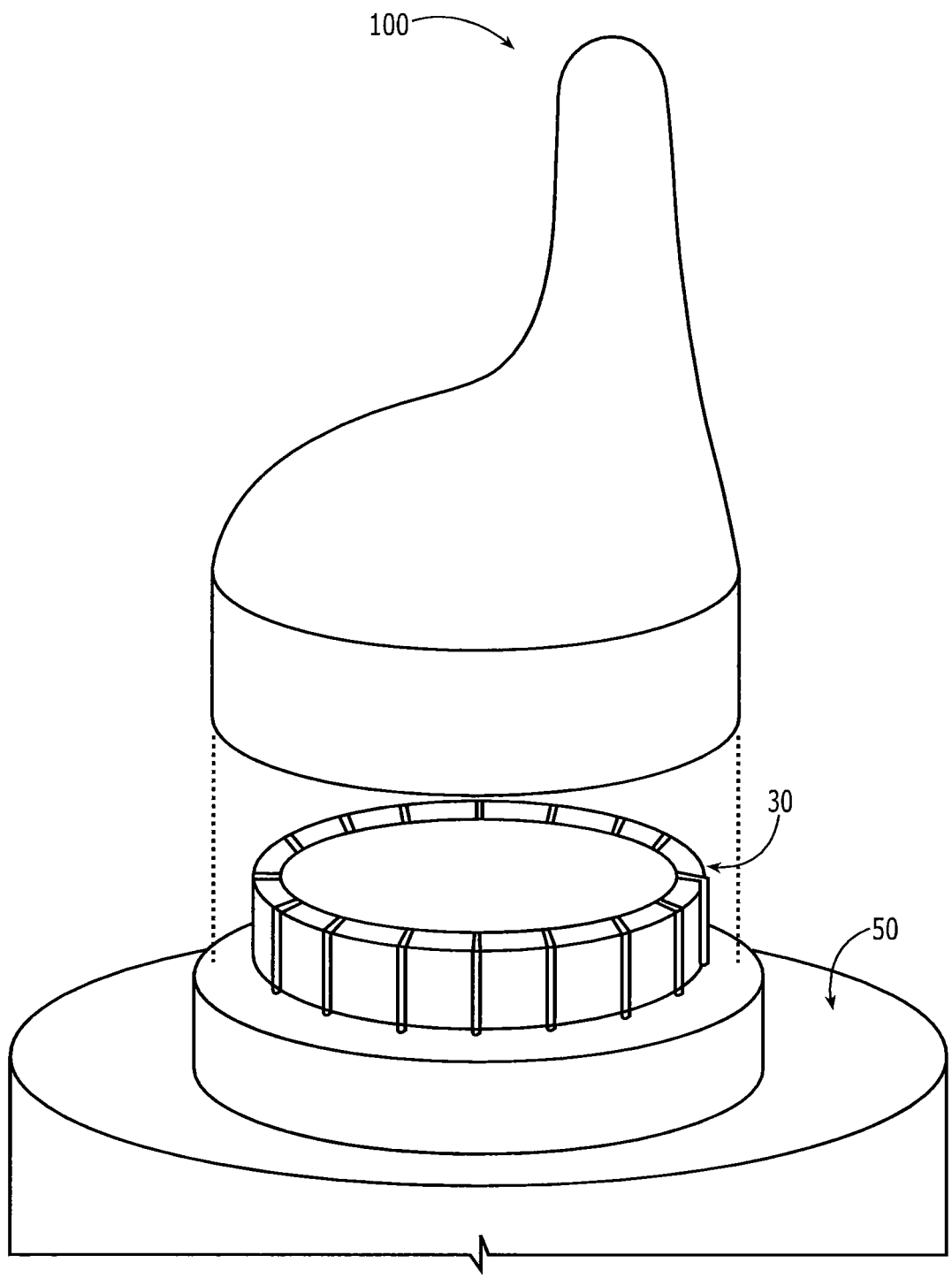
FIG. 9 is an exploded perspective view of the earpiece connecting to the thermoelectric devices (TEDs) and the heat sink of the in-ear stimulator of FIG. 1.
Figure 10:
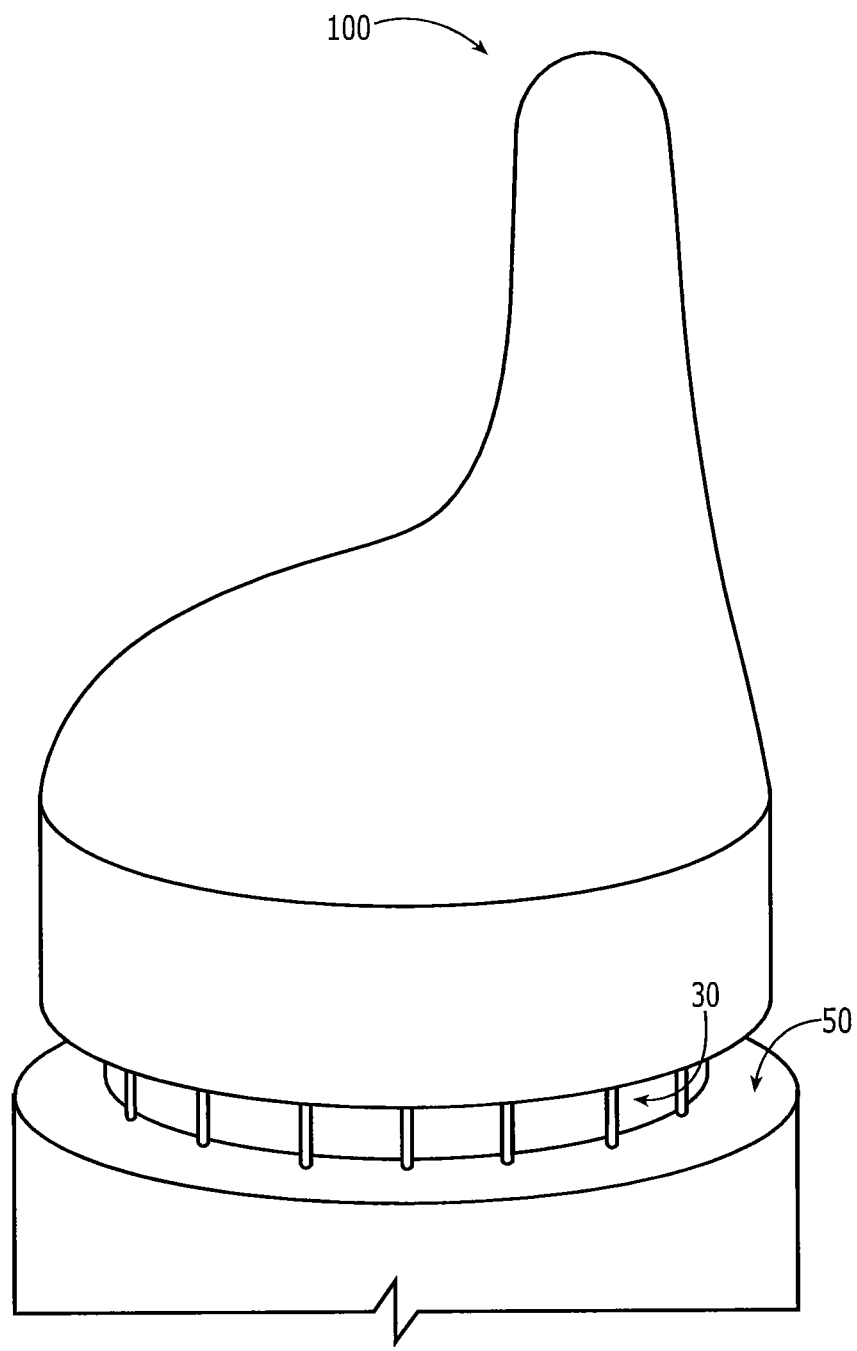
FIG. 10 is an assembled, perspective view of the earpiece connecting to the TEDs (which are arranged in a ring configuration) and the heat sink of the in-ear stimulator of FIG. 9.
Figure 14:
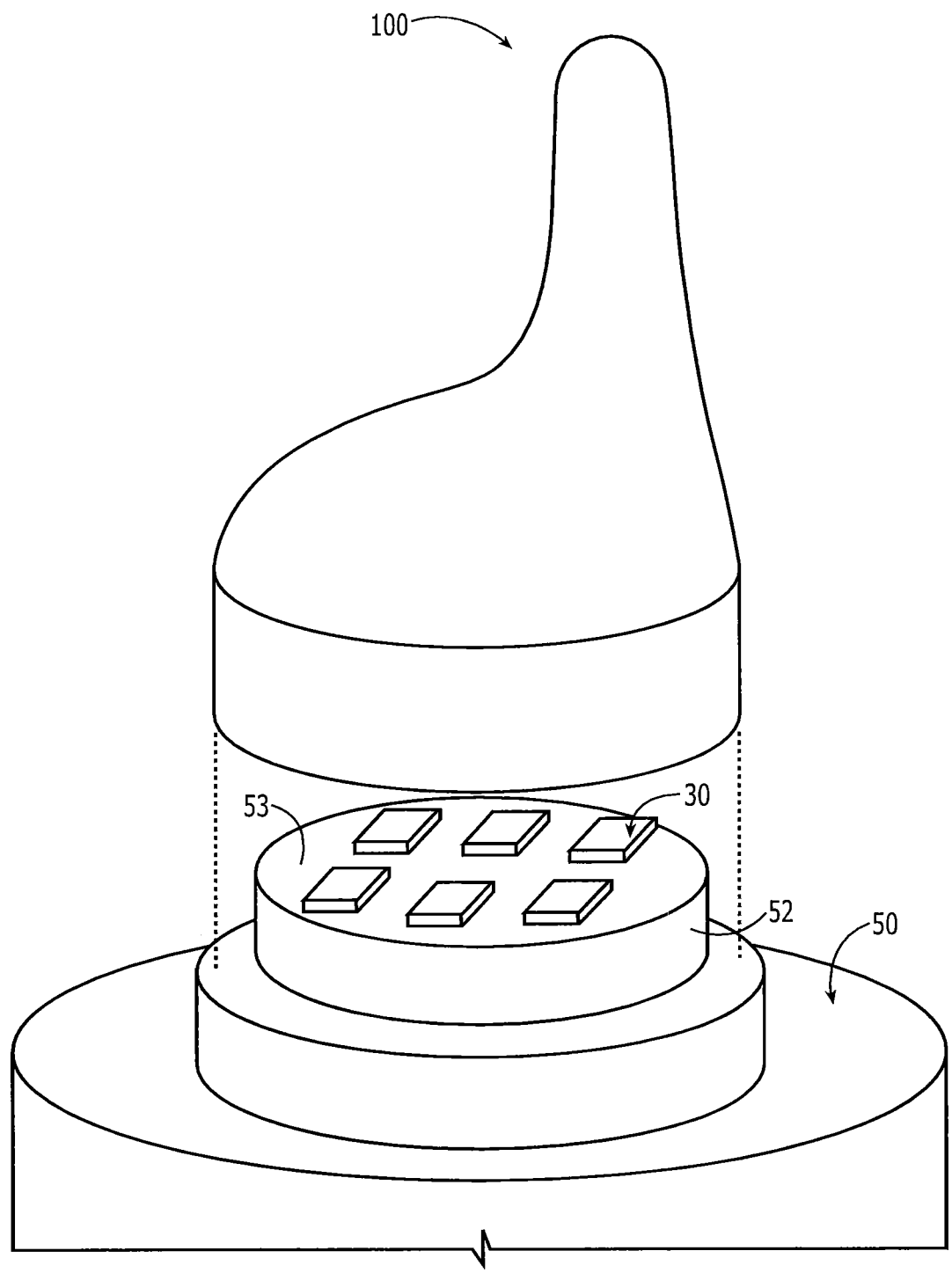
FIG. 14 is an exploded perspective view of an earpiece connecting to TEDs on a platform of the heat sink according to some embodiments of the present invention.
Figure 15:
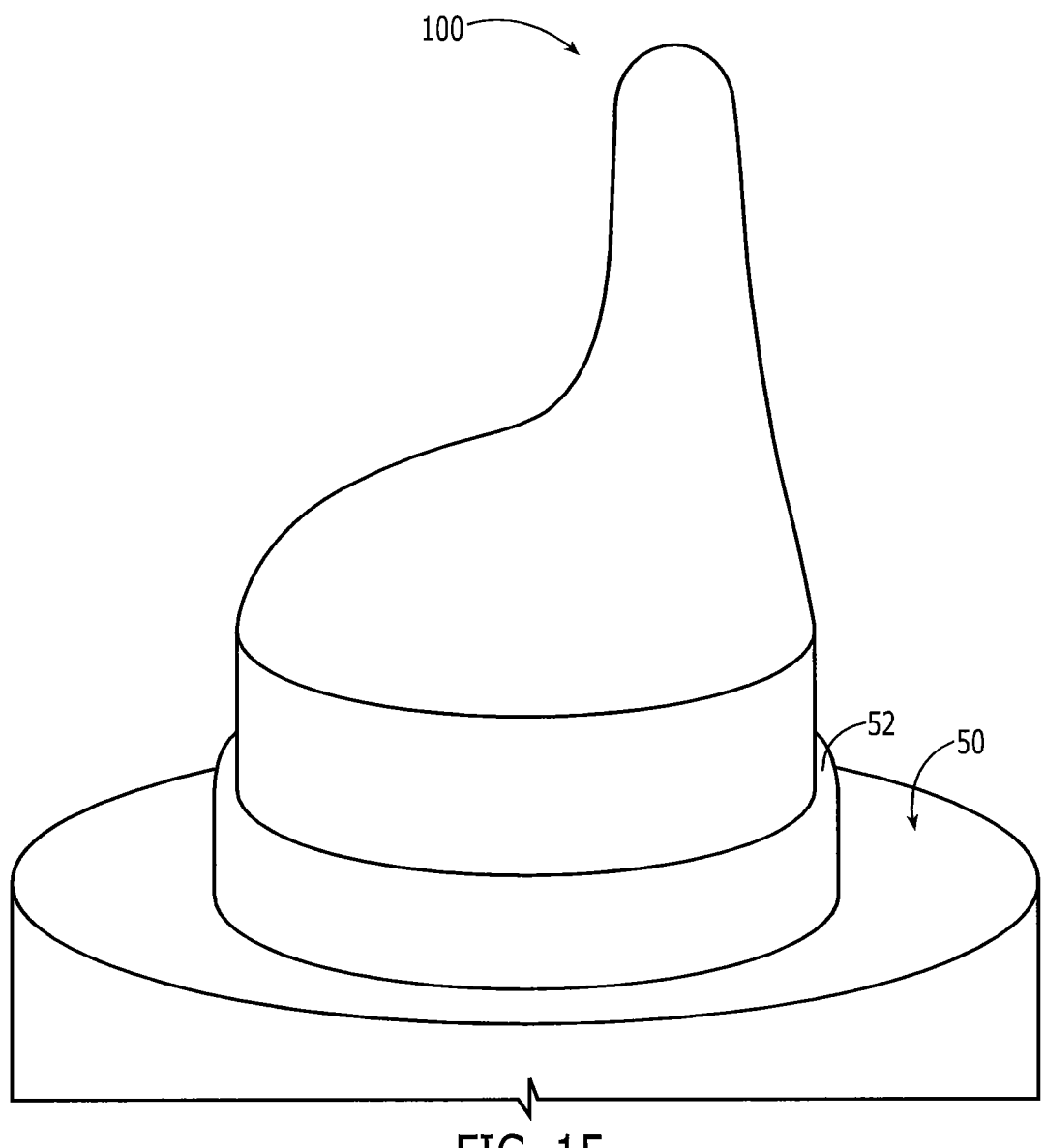
FIG. 15 is an assembled, perspective view of the earpiece and heat sink of FIG. 14.
Figure 16:
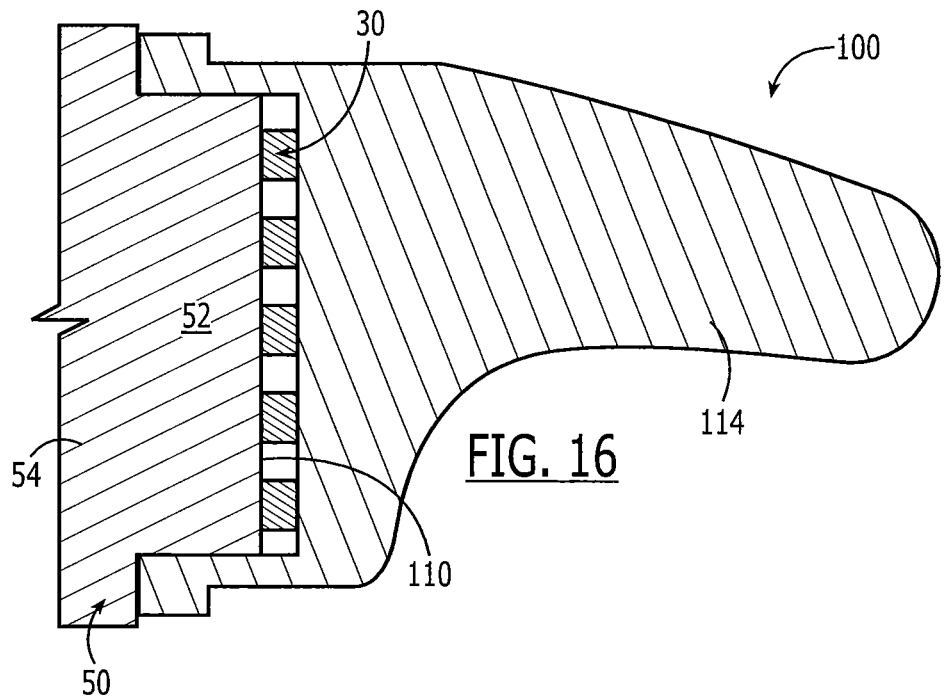
FIG. 16 is a cross-sectional view of the earpiece, TEDs and heat sink of FIG. 14.

As shown in FIG. 5C, the earpiece 100 includes an inner cavity 110 that has an inner surface 112. The cavity 110 may have any suitable shape so that the TEDs may be thermally coupled to the earpiece 100 for increased conductivity. The earpiece 100 may be formed of any suitable material for conducting thermal energy. In particular, the earpiece 100 may be formed of a metal, such as aluminum or an aluminum alloy, e.g., aluminum 7075, which uses zinc as the primary alloying element. In some embodiments, the weight of the earpiece is less than about 12 grams, 9 grams, 6 grams, 4 grams or less. As used herein, "aluminum," includes alloys thereof (e.g., alloys in which aluminum is the predominant metal (typically at least 60, 80 or 90 percent by weight, or more) along with one or more alloying elements such as copper, magnesium, manganese, silicon, and zinc).

In some embodiments, the shape of the earpiece 100 may be customized or semi-customized for an individual wearer. For example, different possible shapes are illustrated in FIGS. 6A-6D, FIGS. 7A-7D and FIGS. 8A-8D, depending on the shape of the subject's ear canal. In some embodiments, at least a portion of the inner surface 112 of the cavity is configured to thermally couple the earpiece 100 to a TED.

As shown in FIGS. 9-12, the earpiece 100 may be connected to a heat sink 50 by TEDs 30. As illustrated, the heat sink 50 is configured to be inserted into the base portion 104 of the earpiece 100; however, the heat sink 50 is thermally isolated from the earpiece 100. The TEDs 30 are configured in a ring shape so that thermal coupling between the TEDs 30 and the base portion 104 of the earpiece 100 may be achieved. The TEDs 30 are also thermally coupled to the heat sink 50 on a side of the TEDs that are opposite to the earpiece 100 so as to create a thermal differential between the heat sink 50 and the earpiece 100. As shown in FIG. 11, the earpiece 100 may be generally hollow so that the inner cavity 110 is only partially filled by a top portion 52 of the heat sink 50, and a base portion 54 of the heat sink extends away from the earpiece 100. The TEDs 30 contact the base portion 104 of the earpiece 100 to thermally couple to the earpiece. The TEDs 30 may be adhered to the base portion 104 of the earpiece using a thermally conductive adhesive, such as silver. It should be understood that the TEDs 30 may be thermally connected to the earpiece 100 and heat sink 50 at any suitable location, including on the bottom rim of the base portion 104 such that the heat sink 50 does not necessarily extend into the earpiece inner cavity 110.

As shown in FIG. 12, the earpiece 100 may be only partially hollow so that the inner cavity 100 is generally filled by the top portion 52 of the heat sink 50. As shown in FIG. 13, the earpiece 100 may include another void or cavity 120. In some embodiments, additional elements, such as a temperature sensor (e.g., an IR temperature sensor) may be positioned in the cavity for detecting the temperature of the earpiece and/or the tissue that the earpiece is heating and/or cooling. In some embodiments, one or more sensors may be either incorporated into the earpiece 100 or provided separately from the earpiece 100 to provide data such as feedback data for analysis to determine, e.g., how an individual subject is responding/reacting to thermal stimulation, which may include measurements of tissue temperatures of the subject. A suitable sensor may be used to sense various parameters of the subject to detect subject response, including but is not limited to, a galvanic skin resistance sensor, a position sensor, a motion detector, a blood pressure sensor, a heart rate sensor, a blood gas level sensor, an electrocardiogram sensor, an electroencephalogram sensor, an electrooculogram sensor, an electronystragmography sensor, a breathing rate sensor, a nystagmus sensor and a temperature sensor. Numerous such sensors are known and can be operatively associated with the systems described herein in accordance with known techniques or variations thereof that will be apparent to those skilled in the art given the present disclosure. See, e.g., U.S. Pat. Nos. 7,578,793; 7,558,622; 7,396,330; 7,215,994; 7,197,357; 7,087,075 and 6,467,905, the disclosure of each of which is incorporated by reference herein in its entirety.

In some embodiments, the circumference of the base 104 may be about 0.82 inches (+/−20%), and the height from the base portion 104 to the tip portion 102 is about 1.13 inches (+/−20%). The inner cavity 110 may extend about 0.25 inches (+/−20%) into the base portion 104 of the earpiece 100 and have a diameter of about 0.70 to 0.75 inches (+/−20%). The diameter of the cavity 120 may be about 0.19 inches (+/−20%).

The earpiece 100 as shown in FIG. 12 includes a sleeve or sheath 130. The sheath 130 may cover and/or may be connected to (e.g., removably connected to, permanently connected to or formed on) the earpiece 100. In some embodiments, the sheath 130 has an inner surface portion configured to conformably engage the earpiece 100, and an outer surface to conformably engage the ear canal of the subject. Hence, heat can be conducted between (that is, to or from) each of the at least one thermoelectric transducers 30 and the ear canal through the sleeve 130 to deliver CVS and/or cranial nerve stimulation to the subject.

In some embodiments, the optional sleeve 130 may comprise areas of high thermal conductivity (high-k) and areas of low thermal conductivity (low-k) such that different portions of the ear canal receive different levels of thermal stimulus (i.e., portions of the ear canal that are adjacent to a low-k area of the sleeve receive a weaker thermal stimulus than portions of the ear canal that are adjacent to a high-k area of the sleeve). In some embodiments, the optional sleeve may comprise only high-k areas or only low-k areas.

In embodiments lacking the optional sleeve 130, the earpiece may similarly comprise high-k and low-k areas whereby portions of the ear canal may be stimulated differentially.

The optional sleeve 130 can comprise, consist of, or consist essentially of any suitable elastic and/or compressible material, such as a polymer, a textile (woven or nonwoven) or a composite thereof. In some embodiments the polymer comprises a hydrogel polymer, a thermally conductive resin, and/or a viscoelastic polymer (it being understood that some but not all viscoelastic polymers will be hydrogel polymers; and some but not all hydrogel polymers will be viscoelastic polymers). Numerous suitable hydrogel polymers, including biodegradable or bioerodable hydrogel polymers, and stable hydrogel polymers (e.g., silicone hydrogel polymers) are known. Examples include but are not limited to those described in U.S. Pat. Nos. 7,213,918; 7,171,276; 7,105,588; 7,070,809; 7,060,051; and 6,960,625. Suitable viscoelastic polymers include but are not limited to those described in, for example, U.S. Pat. Nos. 7,217,203; 7,208,531; and 7,191,483. An ester-based viscoelastic memory foam such as used in the heating pad systems described in U.S. Pat. No. 7,176,419 is among those suitable for use in making sleeves of the present invention. In some embodiments, the optional sleeve 130 has a thermal conductivity of from 0.1 to 50 W/m×K; and a hardness of from 0 to 50 on the Shore A scale.

The optional sleeve 130 can be made by any suitable technique such as molding, casting, etc. While in some preferred embodiments the optional sleeve 130 is removable, in other embodiments that sleeve is formed on, integrally formed with, or otherwise permanently connected to the earpiece 100. The optional sleeve 130 can be open at both the tip portion 102 (closest to the ear drum) and/or the base portion 104. The optional sleeve 130 may be transparent or tinted with a pigment, in whole or in part such as in one or more defined locations on the sleeve (e.g., the medial portion, the outer portion, the upper portion, the lower portion, the front portion, the back portion) to provide an indicator of whether the sleeve is for a left or right ear canal device, an indicator of size of the sleeve, an indicator of how the sleeve should be oriented on the heat sink, etc.

Figure 17:
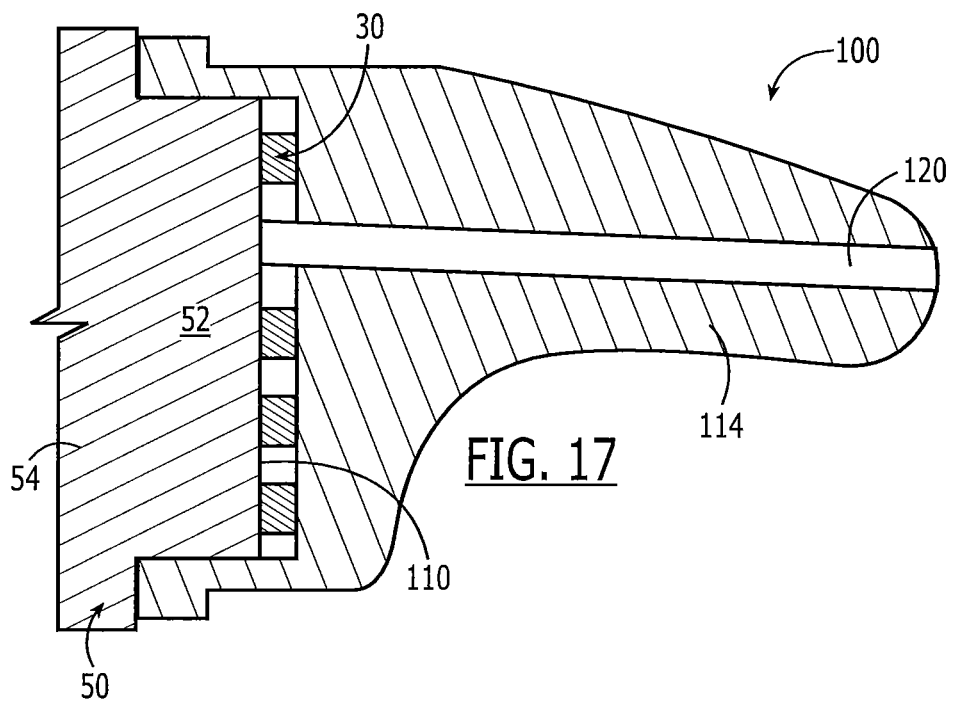
FIG. 17 is a cross-sectional view of an earpiece, TEDs and a heat sink according to some embodiments of the present invention.

As illustrated in FIGS. 14-17, the heat sink 50 may include a generally planar surface 53 that is inserted into the inner cavity 110 of the earpiece 100. The TEDs 30 may be thermally coupled to the earpiece inner surface 112 and to the planar surface 53 of the upper portion 52 of the heat sink 50. As shown in FIG. 17, an additional cavity 120 may be provided for receiving additional elements therein, such as temperature sensors as discussed above.

Figure 18:
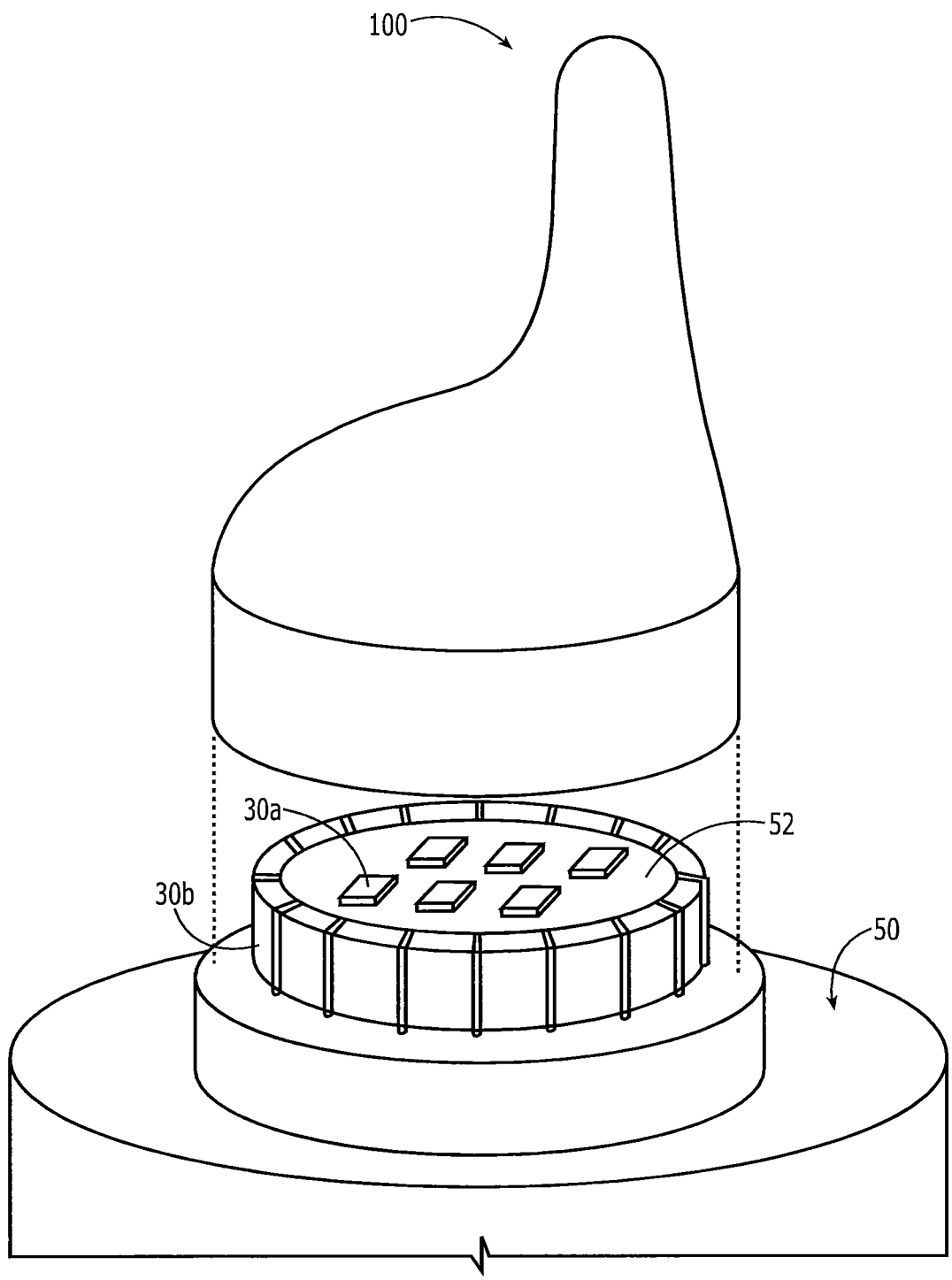
FIG. 18 is an exploded perspective view of an earpiece connecting to TEDs is a ring configuration and on a platform of the heat sink according to some embodiments of the present invention.
Figure 19:
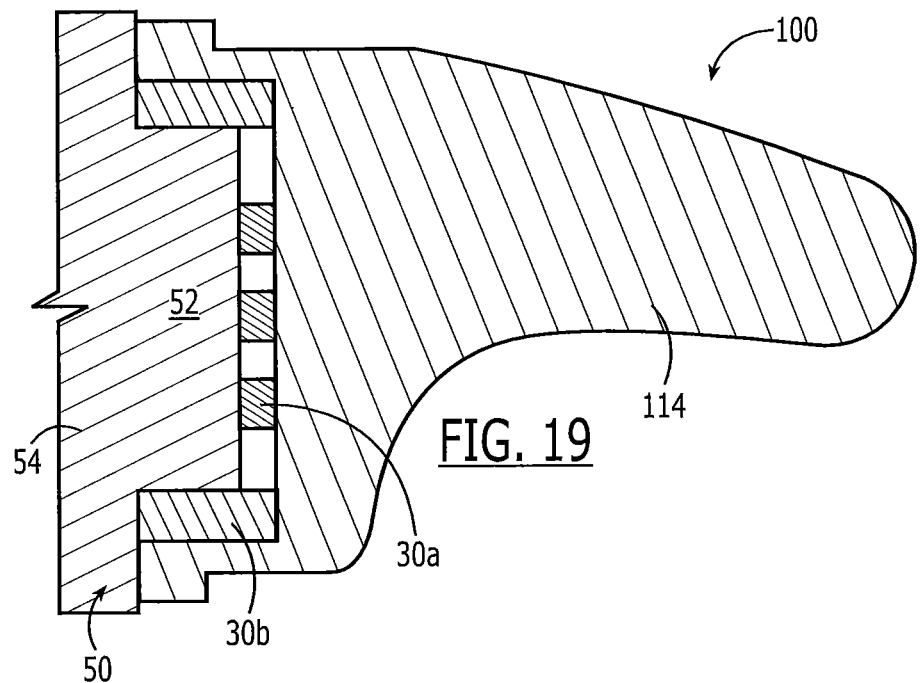
FIG. 19 is a side cross-sectional view of the earpiece, TEDs and heat sink of FIG. 18.
Figure 20:
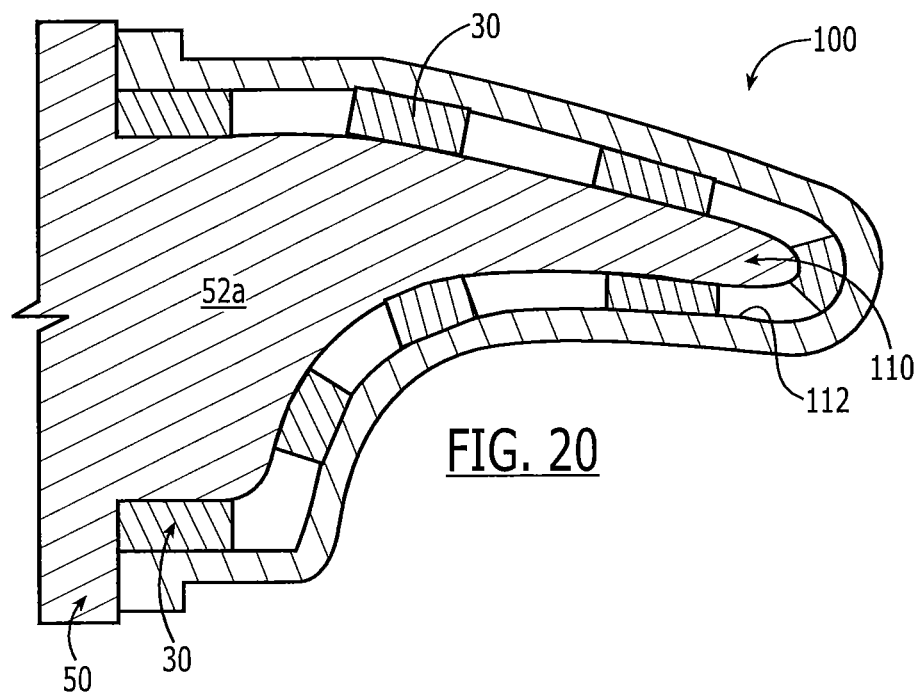
FIG. 20 is a side cross-sectional view of an earpiece, TEDs and heat sink according to some embodiments of the present invention.

As illustrated in FIGS. 18-19, the TEDs 30 may be coupled to the top planar surface 53 and the sides of the top portion 52 of the heat sink 50. As shown in FIG. 20, in some embodiments, the upper portion 52 of the heat sink 50 generally conforms to the inner cavity 110 of the earpiece 100 with the TEDs 30 coupled between the heat sink 50 and the inner surface 112 of the earpiece.

Figure 21A:
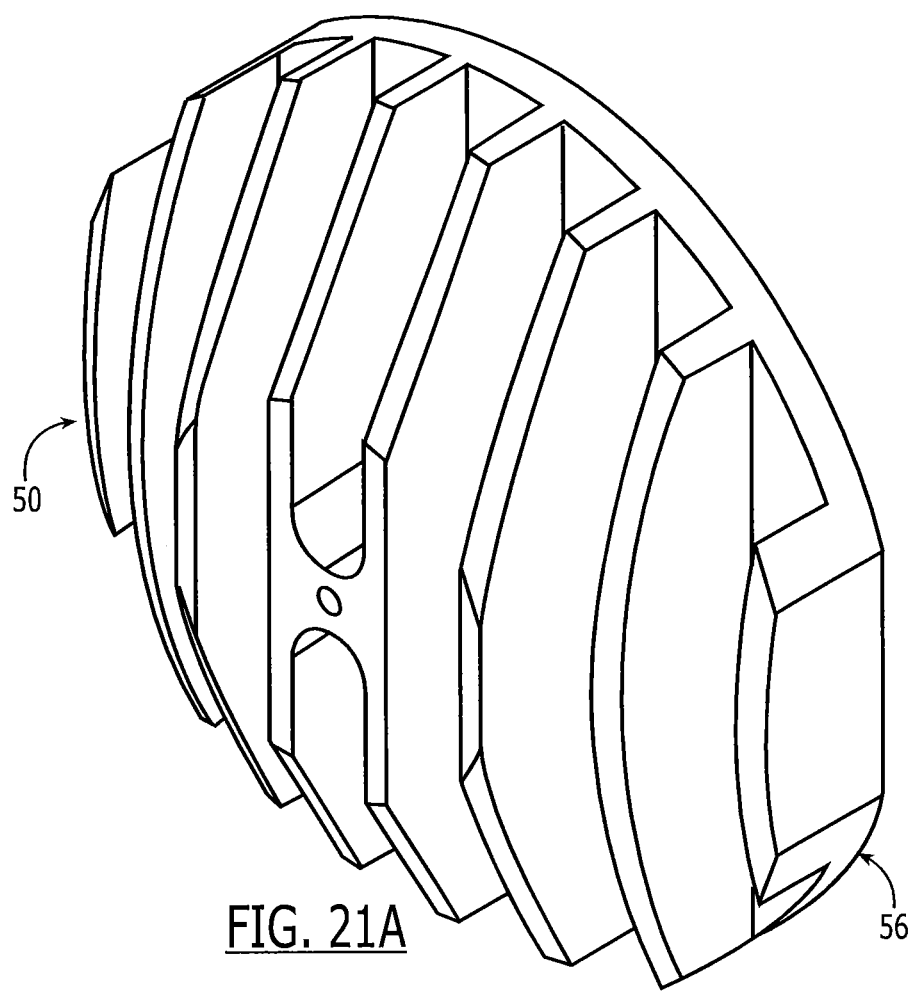
FIG. 21A is a perspective back view of the heat sink of the in-ear stimulation apparatus of FIG. 1.
Figure 21B:
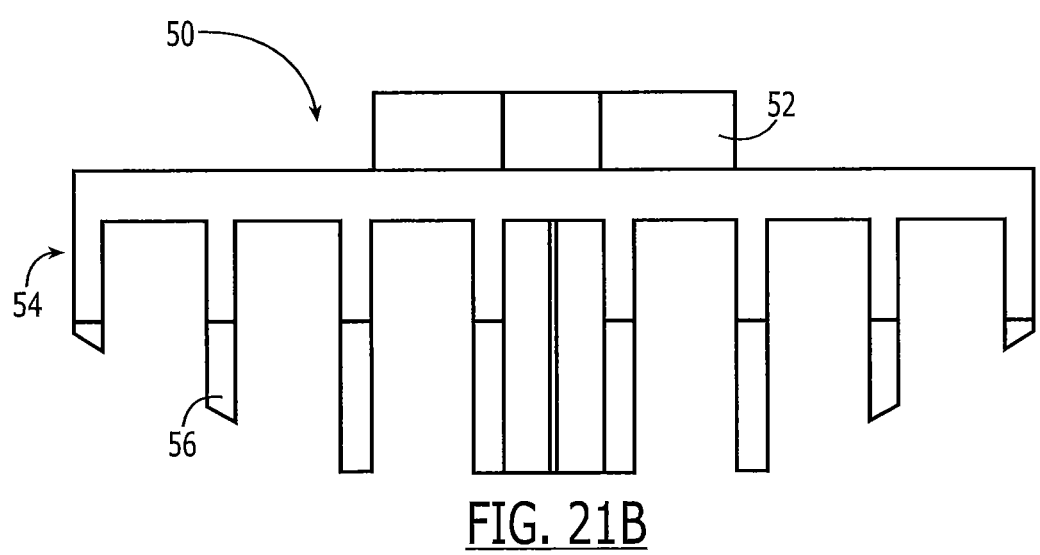
FIG. 21B is a side view of the heat sink of FIG. 21A.

As shown in FIGS. 21A-21B, the heat sink 50 includes an upper portion 52 that is configured to engage the earpiece 100 via the TEDs to thermally couple the earpiece 100 and the heat sink 50. A lower portion 54 of the heat sink 50 includes fins 56 that are spaced apart and configured to dissipate heat and/or cold to the surrounding environment.

In some embodiments, the heat sink 50 is formed of a thermally conductive material, such as a metal (such as aluminum, including alloys thereof (e.g., alloys in which aluminum is the predominant metal (typically at least 60, 80 or 90 percent by weight, or more) along with one or more alloying elements such as copper, magnesium, manganese, silicon, and zinc)). In particular embodiments, aluminum 6061 may be used. The heat sink 50 may weigh between about 30 or 40 grams to about 60 or 70 grams. In particular embodiments, the heat sink 50 weighs about 50-55 grams. The heat sink lower portion 54 may have a diameter of about 2.4 inches (+/−20%). The distance from the top of the lower portion 54 to the distal end of the fins 56 may range from about 0.38 (+/−20%) for the shorter fins 56 on the outer edge of the heat sink 54 to about 0.75 (+/−20%) for the longer fins 56 in the middle of the heat sink 50. As shown, for example, in FIG. 2, the heat sink 50 may be held in position on the headphone 14 by ventilated support members 60 and 62, which include open air vents to further thermal dissipation from the heat sink 50.

In some embodiments, the earpiece 100, TEDs 30 and heat sink 50 may be configured to change the temperature of the earpiece 100 relatively rapidly so that various thermal waveforms may be delivered to the earpiece 100, e.g., due to the thermal conductivity of the materials of the earpiece 100 and heat sink 50, such as the aluminum or aluminum alloys discussed herein. In some embodiments, the slew rate of the earpiece 100 may be about 10° C./minute or about 20° C./minute or less. The temperature of the earpiece 100 in some embodiments may be between about 17° C. to about 46° C., or between about 17° C.-20° C. for cooling the ear canal to about 44° C.-46° C. for warming the ear canal.

Although embodiments according to the present invention are described herein with respect to the earpiece 100, heat sink 50 and TEDs 30, it should be understood that in some embodiments, the earpiece 100 may be omitted and/or the heat sink 50 and earpiece 100 may be combined such that the TEDs 30 are placed in direct contact with the ear canal or are thermally coupled to the ear canal via an optional sleeve. As illustrated in the schematic representation of FIG. 22 (not to scale), the heatsink 50 includes an upper portion 52 that is configured to be inserted into the ear canal and having TEDs 30 mounted thereon. An optional sleeve 130 may be provided, e.g., to increase comfort and wearability. The lower portion 54 of the earpiece 50 may be held in position by a headphone, such as is described herein with respect to the headphone 14 of FIGS. 1-2. In some embodiments, the upper portion 52 of the heat sink 50 is sized and shaped as described herein with respect to the earpiece 100, and the lower portion 54 is sized and shaped as generally described with respect to FIGS. 21A-21B.

Exemplary controllers for controlling the thermal inputs to the TED devices described herein will now be discussed.

Figure 23:
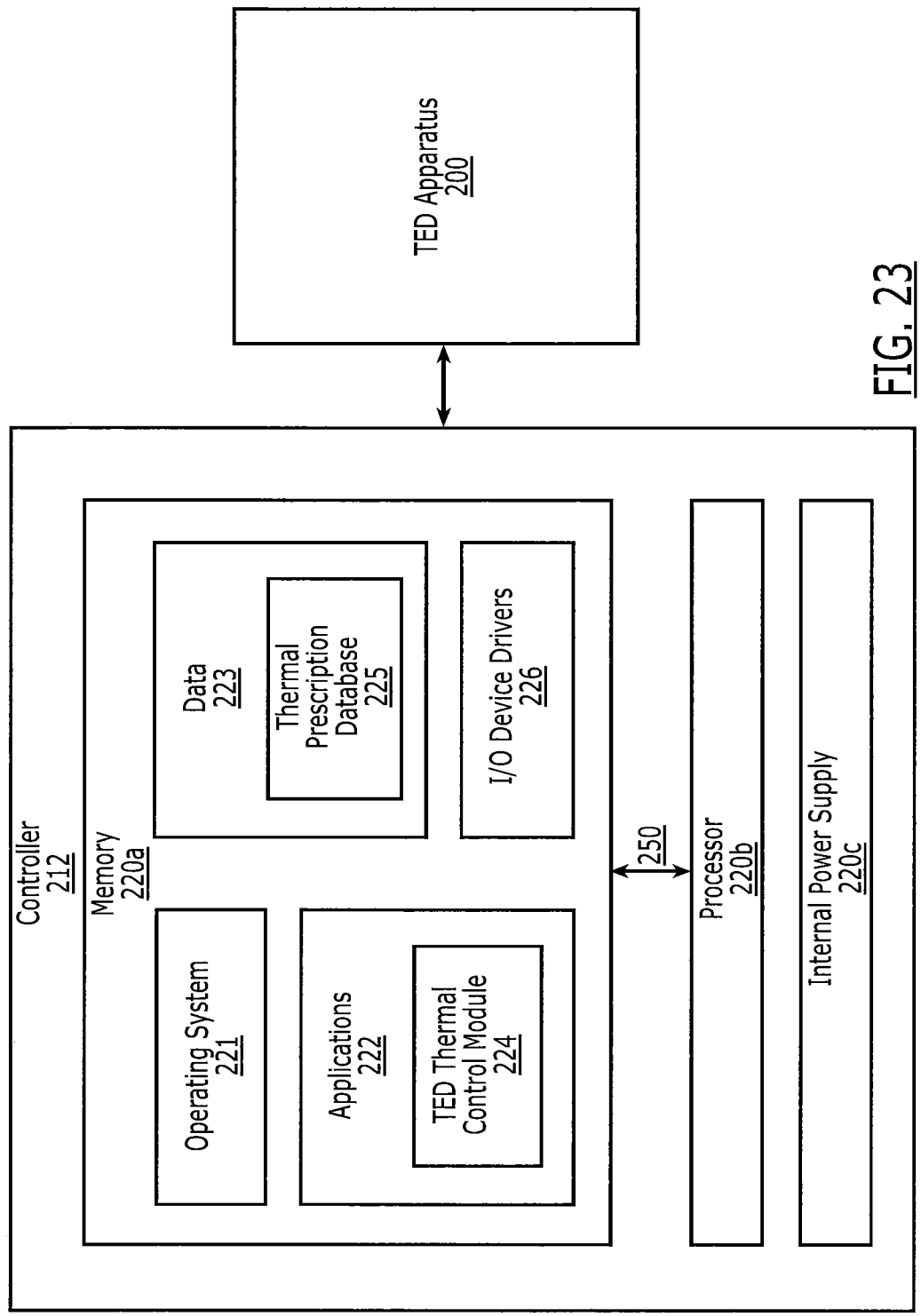
FIG. 23 is a block diagram of an exemplary controller for controlling a thermal variation or waveform to a TED apparatus according to embodiments of the present invention.

FIG. 23 is a block diagram of exemplary embodiments of controllers of the present invention for controlling a TED apparatus 10 to administer various thermal treatment protocols or thermal "prescriptions." As shown in FIG. 23, in some embodiments, the controller 212 comprises memory 220a, a processor 220b and an internal power supply 220c and is operatively and communicatively coupled to a TED apparatus 200 (such as the TED apparatus 10 described herein). The processor 220b communicates with the memory 220a via an address/data bus 250. As will be appreciated by one of skill in the art, the processor 220b may be any commercially available or custom microprocessor. Memory 220a is representative of the overall hierarchy of memory devices containing software and data used to implement the functionality of the controller 212. Memory 220a can include, but it not limited to, the following types of devices: cache, ROM, PROM, EPROM, EEPROM, flash memory, SRAM and DRAM.

As shown in FIG. 23, the controller memory 220a may comprise several categories of software and data: an operating system 221, applications 222, data 223 and input/output (I/O) device drivers 226.

As will be appreciated by one of skill in the art, the controller may use any suitable operating system 221, including, but not limited to, OS/2, AIX, OS/390 or System390 from International Business Machines Corp. (Armonk, N.Y.), Window CE, Windows NT, Windows2003, Windows2007 or Windows Vista from Microsoft Corp. (Redmond, Wash.), Mac OS from Apple, Inc. (Cupertino, Calif.), Unix, Linux or Android.

Applications 222 may comprise one or more programs configured to implement one or more of the various features of the present invention. Applications 222 may comprise a TED thermal control module 224 configured to activate the TED apparatus 200. In some embodiments, the memory 220a comprises additional applications, such as a networking module for connecting to a network. In some embodiments, the control module 224 may be configured to activate at least one TED (i.e., to control the magnitude, duration, waveform and other attributes of stimulation delivered by the at least one TED). In some such embodiments, the control module 224 is configured to activate at least one TED based upon a prescription from the prescription database 225. The thermal prescriptions in the prescription database 225 may include one or more sets of instructions for delivering one or more time-varying thermal waveforms to the vestibular system of a subject. In some such embodiments, the control module 224 is configured to selectively and separately activate a plurality of TEDs (e.g., by activating only one of the plurality of TEDs, by heating one TED and cooling another, by sequentially activating the TEDs, by activating different TEDs using different temperature/timing parameters, combinations of some or all of the foregoing, etc.).

Data 223 may comprise static and/or dynamic data used by the operating system 221, applications 222, I/O device drivers 226 and other software components. Data 223 may comprise a thermal prescription database 225 comprising one or more thermal treatment protocols. In some embodiments, the memory 220a comprises additional data, such as data associated with the delivery of one or more time-varying thermal waveforms, including patient outcomes, temperature measurements of the ear as a result of the thermal stimulation, and the like.

I/O device drivers 226 typically comprise software routines accessed through the operating system 221 by the applications 222 to communicate with devices such as I/O ports, memory 220a components and/or the TED apparatus 200.

In some embodiments, the TED thermal control module 224 is configured to activate at least one TED in the TED apparatus 200 to stimulate the nervous system and/or the vestibular system of a subject. In particular embodiments, the TED thermal control module 224 is configured to activate at least one TED based upon a thermal prescription comprising a set of instructions for delivering one or more time-varying thermal waveforms to the vestibular system of a subject.

In some embodiments, the controller 212 is operatively connected to at least one TED in the TED apparatus 200 via a thermal stimulation conductive line. In some embodiments, the controller 212 is operatively connected to a plurality of TEDs, the controller 212 may be operatively connected to each TED via a separate thermal stimulation conductive line. In some such embodiments, each of the plurality of separate thermal stimulation conductive lines is bundled together into one or more leads (e.g., the thermal stimulation conductive lines connected to the TED(s) thermally coupled to the right earpiece may be bundled separately from the thermal stimulation conductive lines connected to the TED(s) thermally coupled to the left earpiece). In some such embodiments, the thermal stimulation conductive lines are connected to the controller 212 via a lead interface (e.g., one or more leads may be connected to the controller 212 using an 18-pin connector).

In some embodiments, the controller 212 is operatively connected to at least one TED in the TED apparatus 200 via an electrical stimulation conductive line. In some embodiments, the controller 212 is operatively connected to a plurality of TEDs, and the controller may be operatively connected to each TED via a separate electrical stimulation conductive line. In some such embodiments, each of the plurality of separate electrical stimulation conductive lines is bundled together into one or more leads (e.g., two leads, with the conductive lines connected to the TEDs in the right ear being bundled separately from the conductive lines connected to the TEDs in the left ear). In some such embodiments, the electrical stimulation conductive lines are connected to the controller via a lead interface (e.g., two leads may be plugged into the controller using a shared 18-pin connector).

In some embodiments, the controller is operatively connected to at least one TED in the TED apparatus 200 via a wireless connection, such as a Bluetooth connection.

Exemplary thermal waveforms that may be delivered via the TED apparatus 200 as controlled by the controller 212 will now be discussed.

Example 1

Square Wave Administration

A male subject in his forties and good health was administered cold caloric vestibular stimulation to his right ear in a square waveform pattern. The pattern was of cooling to 20 degrees Centigrade (as compared to normal body temperature of about 37 degrees Centigrade) as a "step" function or "square wave" with one symmetric square wave being delivered every two five minutes for a time period of 20 minutes. The subject was observed by others to be slurring his words, and was asked to remain seated for a time of two hours following the treatment session as a precaution. The subject reported a sensation of intoxication, and subsequently reported a sense of "immunity" to the sessions in which square waves cooling was administered for the same and duration.

Example 2

Sawtooth Wave Administration

The same subject that developed a sensation of immunity to the square waveform treatment described in EXAMPLE 1 was subsequently treated by administering cold caloric vestibular stimulation to the right ear in a sawtooth waveform pattern of cooling to 20 degrees Centigrade (as compared to normal body temperature of about 37 degrees Centigrade) in a symmetric sawtooth waveform pattern, without gaps, at a frequency of one cycle or waveform every five minutes, for a total duration of approximately 10 minutes and a delivery of a first and second waveform. Unlike the situation with the square wave pattern described in Example 1, the subject continued to perceive the temperature cycling up and down.

Example 3

Maximum Waveform Amplitude

The same subject described in Examples 1-2 was administered cold caloric vestibular stimulation to the right ear as a sawtooth cooling waveform at different amplitudes in a titration study. A maximum perceived sensation of cyclic cooling was perceived at a peak amplitudes of about 17 degrees Centigrade (or cooling from normal body temperature to a temperature of about 20 degrees Centigrade). Cooling beyond this did not lead to additional gains in the sensation of cyclic cooling perceived by the subject.

Example 4

Minimum Waveform Amplitude

Modeling of the human vestibular system indicates that the cupula (the structure within the semicircular canals pushed by the movement of fluid therein and which contain hair cells that convert the mechanical distortion to electrical signals in the vestibular nerve), is stimulated by caloric vestibular stimulation at chilling temperatures of 5 or 7 degrees Centigrade below body temperature.

Example 5

Maximum Waveform Frequency

Modeling of the human vestibular system indicates that a slew rate faster than 20 degrees Centigrade per minute (which would enable one 20 degree Centigrade waveform every two minutes) is not useful because the human body cannot adapt to temperature changes at a more rapid rate. While maximum frequency is dependent in part on other factors such as waveform amplitude, a maximum frequency of about one cycle every one to two minutes is indicated.

Example 6

Minimum Waveform Frequency

Modeling of the human vestibular system indicates that the a continuous, time-varying waveform is most effective in stimulating the vestibular system, as stagnation and adaptation of the cupula is thereby minimized. While minimum frequency is dependent in part on other factors such as the waveform amplitude, a minimum frequency of about one cycle every ten to twenty minutes is indicated.

Example 7

Treatment Session Duration

To permit delivery of at least a first and second waveform, a duration of at least one or two minutes is preferred. As noted above and below, results have been reported by patients with treatment durations of ten and twenty minutes. Hence, as a matter of convenience, a treatment session duration of not more than 30 or 40 minutes is preferred.

Example 8

Treatment of Migraine Headache with Sawtooth Waveforms

A female patient in her early fifties with a long standing history of migraine suffered an acute migraine episode with symptoms that consisted of a pounding headache, nausea, phonophobia, and photophobia. Right ear cold caloric vestibular stimulation was performed using the sawtooth waveform, essentially as described in Example 2 above, with a temperature maximum of 17 degrees (chilling from body temperature) for 10 minutes (for a total delivery of two cycles). At the conclusion of the treatment the patient reported that her headache and associated symptoms were no longer present. At a reassessment one day later, the patient reported that the headache had not returned.

Example 9

Treatment of Diabetes with Sawtooth Waveforms

The same subject described in examples 1-3 suddenly developed an episode of extreme urination (10 liters per day), thirst for ice water, and associated fatigue. Urinary testing suggested the onset of diabetes mellitus, for which there was strong family history.

The patient's initial weight as taken at his primary care physician indicated a recent 20 pound weight loss. The first attempt to obtain a glucose reading from the patient resulted in an out of range result (this typically occurs with glucose levels in excess of 600 mg/dl). The patient was hospitalized and received hydration and IV insulin therapy. The patient's first glucose level after this treatment was 700 mg/dl. The glucose level were brought down to approximately 350 and treatment with an oral antihyperglycemic agent was initiated.

Follow-up care after hospital discharge with the subject's primary care physician. expanded the oral antihyperglycemic agent therapy to include both metformin and JANUVIA™ sitagliptin. In addition, a strict exercise program of 30-45 minutes 5 to 6 days per week and diet control were instituted. Daily glucose levels via finger stick were taken 2 to 3 times per day.

At this point the patient's baseline hemoglobin A1c (Hb A1c) level was 9.8%, as compared to normal levels of 5 to 6%.

The patient then began daily treatment with caloric vestibular stimulation. The treatment was carried out for a time of ten minutes, once a day for about a month, after which the treatment was continued two to three times a week for three additional months (with each treatment session being about 10 minutes in duration). The caloric vestibular stimulation was delivered to the patient's right ear, as a sawtooth cooling waveform as described in EXAMPLE 2. At the conclusion of these treatments, the patient's HB A1c level was 5.3%. As a result, the patient was removed from all hypoglemic agents.

Most oral antihyperglycemic agents lower a patient's Hb A1c level by approximately 1 to 2% (see generally S. Inzucchi, Oral Antihyperglycemic Therapy for Type 2 Diabetes, JAMA 287, 360-372 (Jan. 16, 2002)). In contrast, this patient's initial value was 9.5, and dropped to 5.3.

Example 10

Alternate Waveform Shapes

Figure 24A:
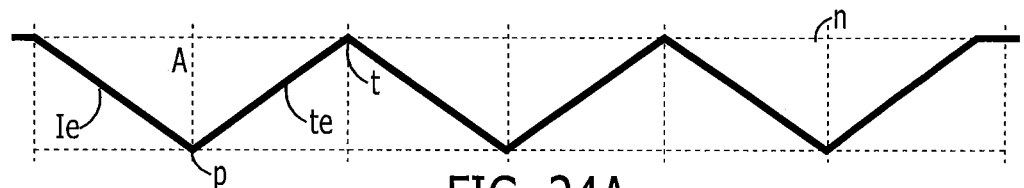
FIGS. 24A-24F are exemplary thermal waveforms that may be administered to the ear canal using a TED apparatus according to some embodiments of the present invention.

The sawtooth waveform described in the examples above was symmetric and linear, as illustrated in FIG. 24A, where line dashed line "n" represents the subject's normal body temperature (typically about 37 degrees Centigrade). Modeling of the vestibular system indicates that waveforms of similar amplitude and frequency, but with a variation in shape, are also effective, such as the "logarithmic" or "convex" waveform of FIG. 24B, and the "exponential" or "concave" waveform of FIG. 4C. All waveforms generally include a leading edge ("le"), a trailing edge ("te"), a peak ("p") and a trough ("t").

Figure 24B:
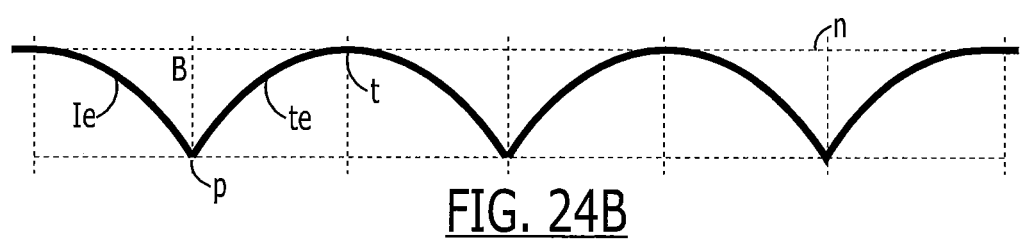
Figure 24C:
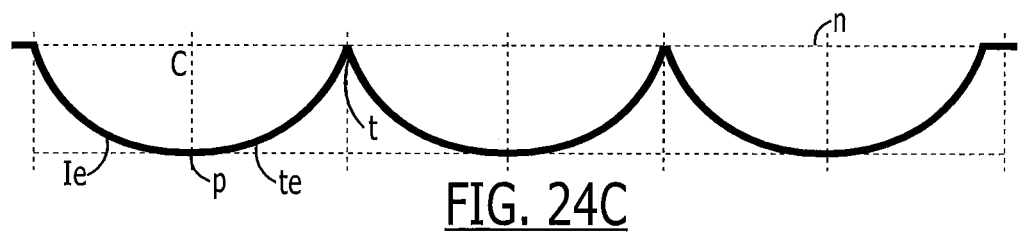
Figure 24D:
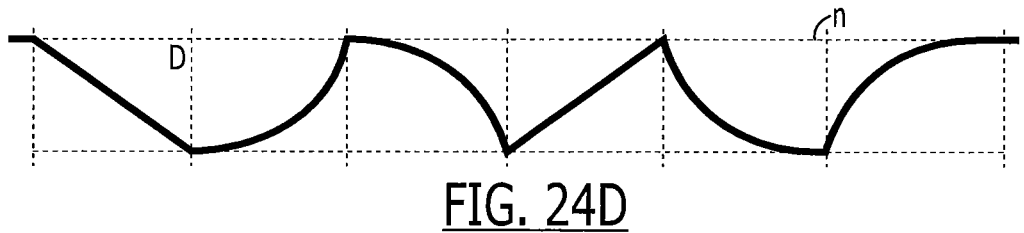

While FIGS. 24A through 24C all show three consecutive waveforms of the same shape, amplitude, and frequency, the consecutive waveforms can be varied in shape as shown in FIG. 4D, and can be varied in amplitude or duration as well (preferably each consecutive waveform within the parameters noted above), to produce still additional waveforms and sequences of waveforms which are useful in carrying out the present invention.

Figure 24E:
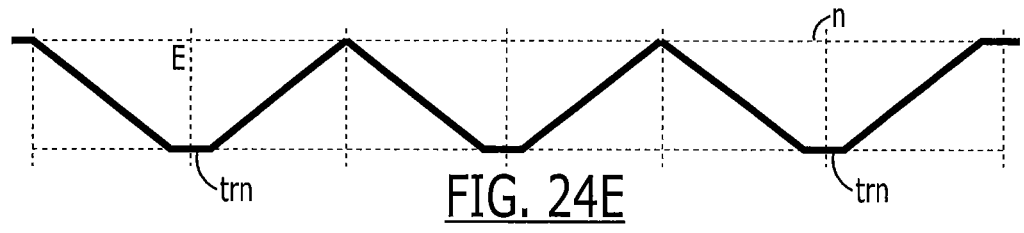
Figure 24F:
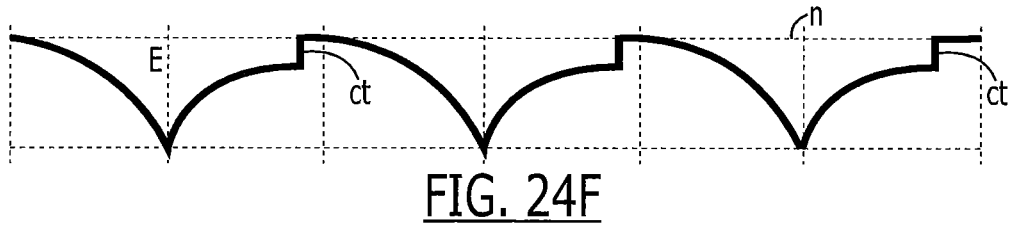

In addition, while the waveforms of FIGS. 24A through 24D are shown as continuous, minor disruptions can be included therein, such as truncations ("trn"; for example, as shown in FIG. 24E) or vertical cuts ("ct"; for example, as shown in FIG. 24F) to produce still additional waveforms and sequences of waveforms which are useful in carrying out the present invention.

The peak for all waveforms of FIGS. 24A-24F is cooling by 17 degrees Centigrade from normal body temperature to a temperature of 20 degrees Centigrade, and the trough for all waveforms is a return to normal body temperature, giving an amplitude of 17 degrees Centigrade. The frequency for all illustrated waveforms is 1 cycle (or one complete waveform) every five minutes. While 3 cycles of the same waveform are illustrated for clarity, note that in some of the examples above only two cycles are delivered over a total treatment or session duration of ten minutes.

Example 11

Patient Orientation

It was noted that a patient who was sitting up (watching TV) and receiving a cold caloric vestibular stimulation (CVS) treatment reported perceiving a different effect than perceived in prior sessions. Upon reclining to about 45 degrees, she did.

The "standard" angle of recline for diagnostic CVS is about 60 degrees (or equivalently 30 degrees above horizontal). The reason for this positioning is that the "horizontal" SCC is actually tilted up by about 30 degrees (higher on rostral side). The intent with diagnostic CVS is to reorient the horizontal SCC so that it is substantially vertical, thus maximizing the effect of the convective flow set up by calorics.

Hence, if the subject is reclined to about 30 degrees above horizontal (and supine), then a cold stimulus leads to inhibition or a phasic rate less than the tonic rate. For a warm stimulus, this is reversed (phasic rate increases above tonic).

Further, cold simulation tends to activate principally the contralateral brain structures whereas hot leads to prinicpally ipsilateral activation. For example, in the fMRI paper by V. Marcelli et al. (Eur. J. Radiol. 70(2): 312-6 (2009) (epub Mar. 14, 2008), the authors did a left ear, cold stimulation by water irrigation and saw right-side activation in the brainstem, cerebellum, etc. The patient was presumably nearly reclined in the MRI magnet.

Empirical tests and modeling indicate that approximately 20 degrees Centigrade absolute cooling (17 degrees Centigrade below body temp) is the lower limit beyond which the cupula is maximally deformed and therefore the phasic rate change is maximal. On the warming side, more than about 7 degrees above body temp becomes uncomfortable. This will not lead to maximal deformation of the cupula. Therefore, there is an asymmetry in terms of ability to span the full frequency spectrum of phasic firing rates. Specifically, one can't access the highest frequencies through use of warm stimulation due to the inability to use overly warm stimulus on a patient.

However, this is not an immutable issue. Since inverting the patient changes the sign of the inhibitory/excitatory motion of the cupula, the following can be seen: Using a cold stimulus, of 20 degrees absolute, but now orient the patient so that his head is tilted forward by 75-120 degrees from vertical. This will invert the horizontal SCC relative to the image above and now the cold stimulus will result in an excitatory increase in the phasic firing rate. For clarity, tilting the head forward by 30 degrees makes the horizontal SCC substantially horizontal. Tilting beyond that now starts to invert it so that at 120 degrees (tilted forward), the horizontal SCC will be in a vertical orientation, but now 180 degrees flipped from what is used in conventional diagnostic caloric vestibular stimulation. So, the "general rule" for treatment of having the patient reclined by 45-90 degrees can be expanded to include "tilted forward" by 75-120 degrees.

Thus a protocol is seen where, using only cold stimulus, one can cover the entire range of phasic firing rates simply by reorienting the patient at the appropriate points during the time course of treatment.

Note that this type inversion should also lead to an inversion in the side of the brain that is primarily activated. Specifically, if cold stimulation leads principally to contralateral activation in the "rightside up" orientation, then it should lead to principally ipsilateral activation in the "upside down" orientation.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are That which is claimed:

1. An in-ear stimulator for administering thermal stimulation to the ear canal of a subject, comprising:
(a) an earpiece configured to be insertable into the ear canal of said subject, said earpiece having an outer surface and an internal cavity formed therein, said internal cavity having an inner surface; and
(b) at least one thermoelectric device thermally coupled to said earpiece internal cavity inner surface; and
(c) a controller configured to deliver a time-varying thermal waveform to said at least one thermoelectric device such that said thermoelectric device effects corresponding temperature changes to said earpiece to deliver caloric stimulation to the subject, wherein the controller is configured to deliver the time-varying thermal waveform such that the time-varying thermal waveform comprises an amplitude that increases or decreases through a plurality of different temperature points over time,
wherein the subject is afflicted with a condition and the vestibular stimulation is configured to provide a therapeutic effect for treatment of the condition.

2. The stimulator of claim 1, wherein the vestibular stimulation is configured to provide acute treatment of the condition.

3. The stimulator of claim 1, wherein the subject is afflicted with a condition and the vestibular stimulation is configured to provide chronic treatment of the condition.

4. The stimulator of claim 1, wherein the condition comprises Parkinson's disease.

5. The stimulator of claim 1, wherein the condition comprises headache.

6. The stimulator of claim 1, wherein the condition comprises brain injury.

7. The stimulator of claim 1, further comprising a heat sink thermally coupled to said at least one thermoelectric device.

8. The stimulator of claim 1, wherein the at least one thermoelectric device is positioned in the internal cavity.

9. The stimulator of claim 1, wherein said at least one thermoelectric device comprises a thin film thermoelectric device.

10. A method for delivering caloric stimulation to a subject, wherein the subject is afflicted with a condition and the vestibular stimulation is configured to provide a therapeutic effect for treatment of the condition, the method comprising:
providing an in-ear stimulator comprising:
(a) an earpiece configured to be insertable into the ear canal of said subject, said earpiece having an outer surface and an internal cavity formed therein, said internal cavity having an inner surface;
(b) at least one thermoelectric device positioned in the internal cavity and thermally coupled to said earpiece internal cavity inner surface; and
(c) a controller configured to deliver a time-varying thermal waveform to said at least one thermoelectric device such that said thermoelectric device effects corresponding temperature changes to said earpiece to deliver caloric stimulation to the subject;
positioning at least a portion of an in-ear stimulator in an ear canal of the subject; and
delivering the time-varying thermal waveform controlled by the controller such that the time-varying thermal waveform comprises an amplitude that increases or decreases through a plurality of different temperature points over time to thereby provide a therapeutic effect for treatment of the condition.

11. The method of claim 10, wherein the vestibular stimulation is configured to provide acute treatment of the condition.

12. The method of claim 10, wherein the subject is afflicted with a condition and the vestibular stimulation is configured to provide chronic treatment of the condition.

13. The method of claim 10, wherein the condition comprises Parkinson's disease.

14. The method of claim 10, wherein the condition comprises headache.

15. The method of claim 10, wherein the condition comprises brain injury.

16. The method of claim 10, further comprising a heat sink thermally coupled to said at least one thermoelectric device.

17. The method of claim 10, wherein the at least one thermoelectric device is positioned in the internal cavity.

18. The method of claim 10, wherein said at least one thermoelectric device comprises a thin film thermoelectric device.

* * * * *